US010304275B2

(12) United States Patent
Dyne et al.

(10) Patent No.: US 10,304,275 B2
(45) Date of Patent: May 28, 2019

(54) TRIGGERED NEURAL GATE INTERFACE

(71) Applicant: Cubic Corporation, San Diego, CA (US)

(72) Inventors: Mark Dyne, Croydon (GB); Steffen Reymann, Guildford (GB)

(73) Assignee: Cubic Corporation, San Diego, CA (US)

(*) Notice: Subject to any disclaimer, the term of this patent is extended or adjusted under 35 U.S.C. 154(b) by 0 days.

(21) Appl. No.: 16/170,565

(22) Filed: Oct. 25, 2018

(65) Prior Publication Data

US 2019/0122475 A1 Apr. 25, 2019

Related U.S. Application Data

(60) Provisional application No. 62/577,069, filed on Oct. 25, 2017.

(51) Int. Cl.
*G07C 9/02* (2006.01)
*G07C 9/00* (2006.01)
*G06F 3/01* (2006.01)

(52) U.S. Cl.
CPC .............. *G07C 9/02* (2013.01); *G06F 3/015* (2013.01); *G07C 9/00126* (2013.01)

(58) Field of Classification Search
CPC ........ G07C 9/02; G07C 9/00126; G06F 3/015
See application file for complete search history.

(56) References Cited

U.S. PATENT DOCUMENTS

| 5,837,982 | A  | 11/1998 | Fujioka  |
| 6,928,354 | B2 | 8/2005  | Ryu      |
| 8,095,209 | B2 | 1/2012  | Flaherty |
| 9,317,976 | B2 | 4/2016  | Andrews et al. |
| 9,501,768 | B2 | 11/2016 | Ho et al. |
| 9,563,273 | B2 | 2/2017  | Mann     |

(Continued)

FOREIGN PATENT DOCUMENTS

| EP | 3087912 A1    | 11/2016 |
| WO | 2005-004067 A1 | 1/2005 |

OTHER PUBLICATIONS

International Search Report and Written Opinion dated Jan. 28, 2019 for International Patent Application No. PCT/US2018/057486 filed Oct. 25, 2018, all pages.

*Primary Examiner* — Mohamed Barakat
(74) *Attorney, Agent, or Firm* — Kilpatrick Townsend & Stockton

(57) ABSTRACT

A wearable electronic device comprising an electroencephalography (EEG) sensor for enabling access to a transit system. The device may also include a device transmitter configured to wirelessly transmit request signals to a transit gate. The device may further include a device processor configured to receive a first EEG signal from the EEG sensor and analyze the first EEG signal to determine that the transit user is attempting to enter the transit system through a particular transit gate. The device processor may also receive a second EEG signal and analyze the second EEG signal to determine that the transit user is currently passing through the particular gate. The first EEG signal may be based on the transit user viewing a visual stimulus displayed by the transit gate, and the second EEG signal may be based on the transit user hearing an auditory stimulus outputted by the transit gate.

20 Claims, 19 Drawing Sheets

(56) References Cited

U.S. PATENT DOCUMENTS

| | | | |
|---|---|---|---|
| 9,972,149 B2* | 5/2018 | Busch-Sorensen | ............................ G07C 9/00111 |
| 9,986,933 B2 | 6/2018 | Nutaro et al. | |
| 10,096,181 B2* | 10/2018 | Reymann | ................. E05F 15/76 |
| 10,109,128 B2* | 10/2018 | Kuraoka | ................... B25J 19/06 |
| 10,121,297 B2* | 11/2018 | Busch-Sorensen | ............................ G07C 9/00111 |
| 2008/0229408 A1 | 9/2008 | Dinges et al. | |
| 2009/0063866 A1 | 3/2009 | Navratil et al. | |
| 2010/0234752 A1 | 9/2010 | Sullivan et al. | |
| 2010/0280958 A1* | 11/2010 | Hasson | ................... G06Q 20/40 705/75 |
| 2013/0018705 A1 | 1/2013 | Heath et al. | |
| 2013/0127708 A1 | 5/2013 | Jung et al. | |
| 2015/0077218 A1* | 3/2015 | Chakkaew | ......... G07C 9/00126 340/5.2 |
| 2015/0272496 A1 | 10/2015 | Klappert et al. | |
| 2016/0060944 A1 | 3/2016 | Perkins et al. | |
| 2016/0171805 A1* | 6/2016 | Jang | ................... G07C 9/00158 382/118 |
| 2017/0061715 A1 | 3/2017 | Busch-Sorensen et al. | |
| 2018/0298690 A1* | 10/2018 | May | ........................ E06B 11/08 |

* cited by examiner

TRIGGERED NEURAL GATE INTERFACE

CROSS-REFERENCES TO RELATED APPLICATIONS

This Application claims priority to U.S. Provisional Patent Application No. 62/577,069 filed Oct. 25, 2017 titled "TRIGGERED NEURAL GATE INTERFACE," the entire disclosure of which is hereby incorporated by reference, for all purposes, as if fully set forth herein. This Application is related to U.S. Non-Provisional patent application Ser. No. 16/019,242 filed Jun. 26, 2018 titled "SYSTEM AND METHOD FOR TRANSIT ACCESS USING EEG SENSORS," the entire disclosure of which is hereby incorporated by reference, for all purposes, as if fully set forth herein.

BACKGROUND OF THE INVENTION

As populations in the world's largest cities continue to grow, often at an exponential rate, public and private transportation systems are becoming increasingly burdened with increased ridership and transit stations are becoming increasingly congested, causing delays to transit users and increased costs to the transportation systems. The use of sophisticated communication devices presents an appealing approach for managing such overcrowding.

Unfortunately, existing devices and approaches are insufficient to alleviate these problems. Accordingly, new systems, methods, and other techniques are needed.

BRIEF SUMMARY OF THE INVENTION

A summary of the invention is described in reference to one or more examples listed below. As used below, any reference to a series of examples is to be understood as a reference to each of those examples disjunctively (e.g., "Examples 1-4" is to be understood as "Examples 1, 2, 3, or 4").

Example 1 is a wearable electronic device for enabling access to a transit system, the wearable electronic device comprising: an electroencephalography (EEG) sensor configured to detect EEG signals corresponding to a transit user; a device transmitter configured to transmit wireless signals to a gate receiver of a transit gate; and a device processor configured to perform operations comprising: receiving, from the EEG sensor, a first EEG signal based at least in part on the transit user viewing a visual stimulus associated with the transit gate; analyzing the first EEG signal to determine that the transit user is attempting to enter the transit system through the transit gate; transmitting, to the gate receiver via the device transmitter, a first wireless signal indicating that the transit user is attempting to enter the transit system through the transit gate; receiving, from the EEG sensor, a second EEG signal based at least in part on the transit user hearing an auditory stimulus associated with the transit gate; analyzing the second EEG signal to determine that the transit user is passing through the transit gate; and transmitting, to the gate receiver via the device transmitter, a second wireless signal indicating that the transit user is passing through the transit gate.

Example 2 is the wearable electronic device of example(s) 1, wherein the transit gate is configured to allow the transit user to enter the transit system in response to receiving the second wireless signal by removing a physical barrier associated with the transit gate.

Example 3 is the wearable electronic device of example(s) 1-2, wherein the first wireless signal is transmitted concurrently with the second wireless signal.

Example 4 is the wearable electronic device of example(s) 1-3, wherein the visual stimulus is displayed via a display system located at the transit gate.

Example 5 is the wearable electronic device of example(s) 1-4, wherein the auditory stimulus is outputted via an audio system located at the transit gate.

Example 6 is the wearable electronic device of example(s) 1-5, wherein the transit gate is configured to output the auditory stimulus via the audio system in response to receiving the first wireless signal.

Example 7 is the wearable electronic device of example(s) 1-6, wherein the operations further comprise: receiving a stimuli timing signal containing timing information corresponding to one or both of the visual stimulus and the auditory stimulus.

Example 8 is a method of enabling access to a transit system, the method comprising: receiving, from an electroencephalography (EEG) sensor, a first EEG signal based at least in part on a transit user viewing a visual stimulus associated with a transit gate; analyzing the first EEG signal to determine that the transit user is attempting to enter the transit system through the transit gate; transmitting a first wireless signal indicating that the transit user is attempting to enter the transit system through the transit gate; receiving, from the EEG sensor, a second EEG signal based at least in part on the transit user hearing an auditory stimulus associated with the transit gate; analyzing the second EEG signal to determine that the transit user is passing through the transit gate; and transmitting a second wireless signal indicating that the transit user is passing through the transit gate.

Example 9 is the method of example(s) 8, wherein the transit gate is configured to allow the transit user to enter the transit system in response to receiving the second wireless signal by removing a physical barrier associated with the transit gate.

Example 10 is the method of example(s) 8-9, wherein the first wireless signal is transmitted concurrently with the second wireless signal.

Example 11 is the method of example(s) 8-10, wherein the visual stimulus is displayed via a display system located at the transit gate.

Example 12 is the method of example(s) 8-11, wherein the auditory stimulus is outputted via an audio system located at the transit gate.

Example 13 is the method of example(s) 8-12, wherein the transit gate is configured to output the auditory stimulus via the audio system in response to receiving the first wireless signal.

Example 14 is the method of example(s) 8-13, further comprising: receiving a stimuli timing signal containing timing information corresponding to one or both of the visual stimulus and the auditory stimulus.

Example 15 is a transit gate comprising: a gate receiver configured to receive wireless signals from a wearable electronic device, wherein the wearable electronic device includes an electroencephalography (EEG) sensor configured to detect EEG signals corresponding to a transit user; a display system configured to display a visual stimulus, wherein the wearable electronic device is configured to determine that the transit user is attempting to enter a transit system through the transit gate based on a first EEG signal detected by the EEG sensor, the first EEG signal based at least in part on the transit user viewing the visual stimulus; an audio system configured to output an auditory stimulus, wherein the wearable electronic device is configured to determine that the transit user is passing through the transit gate based on a second EEG signal detected by the EEG sensor, the second EEG signal based at least in part on the transit user hearing the auditory stimulus; and a gate processor configured to perform operations comprising: receiving, via the gate receiver from the wearable electronic device, a first wireless signal indicating that the transit user is attempting to enter the transit system through the transit gate; and receiving, via the gate receiver from the wearable electronic device, a second wireless signal indicating that the transit user is passing through the transit gate.

Example 16 is the transit gate of example(s) 15, wherein the operations further comprise: in response to receiving the second wireless signal, allowing the transit user to enter the transit system by removing a physical barrier associated with the transit gate.

Example 17 is the transit gate of example(s) 15-16, wherein the first wireless signal is received concurrently with the second wireless signal.

Example 18 is the transit gate of example(s) 15-17, wherein the operations further comprise: outputting, via the audio system, the auditory stimulus.

Example 19 is the transit gate of example(s) 15-18, wherein the auditory stimulus is outputted in response to receiving the first wireless signal.

Example 20 is the transit gate of example(s) 15-19, wherein the operations further comprise: receiving a stimuli timing signal containing timing information corresponding to one or both of the visual stimulus and the auditory stimulus.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

FIG. 7 illustrates an example of the analysis performed by a device processor in determining which gate a transit user is attempting to enter a transit system through.

FIG. 9 illustrates an example of the analysis performed by a device processor in determining which gate a transit user is attempting to enter a transit system through.

Figure 1:
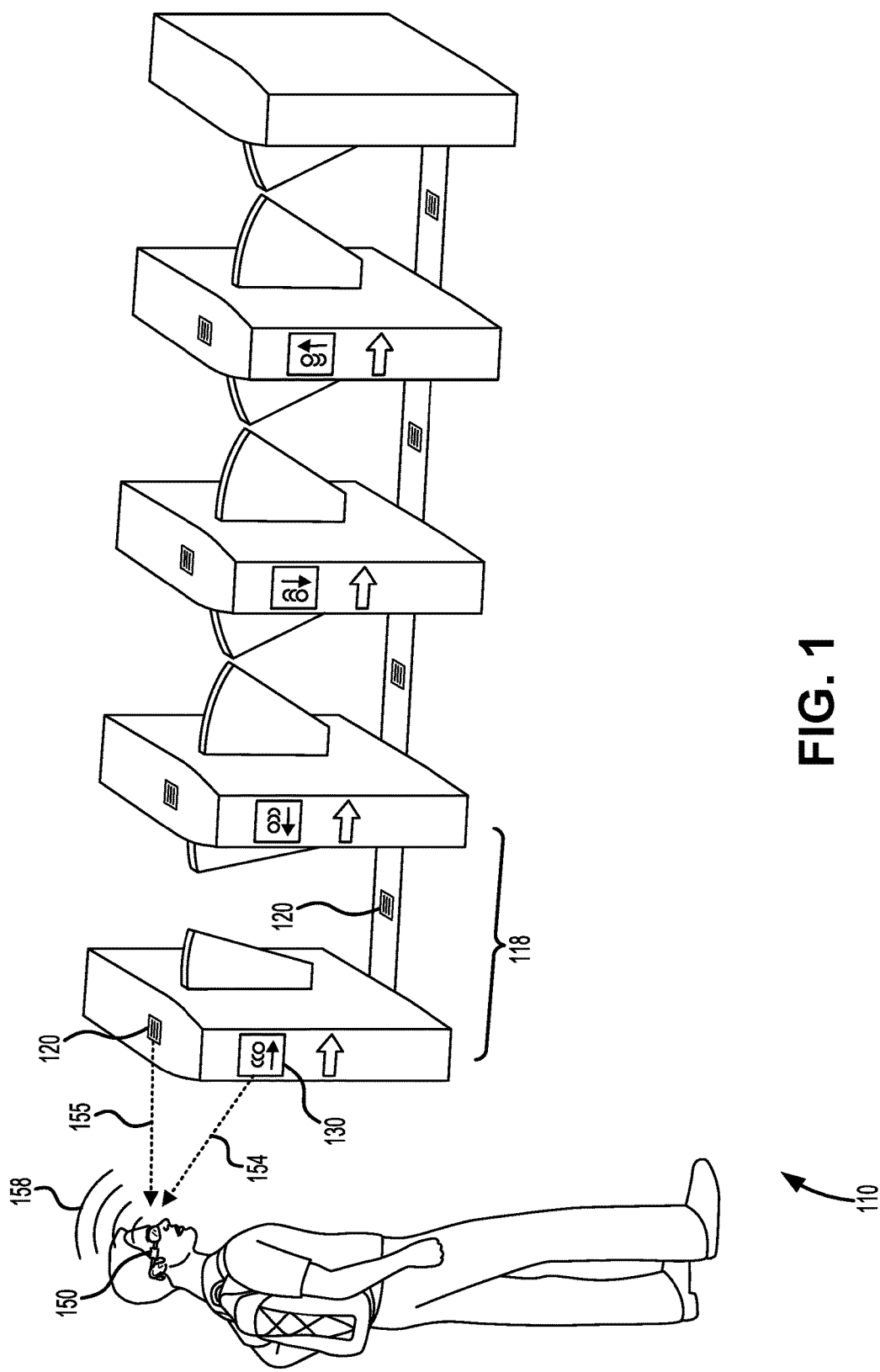
FIG. 1 illustrates an example according to the present invention in which a transit user gains entry to a transit system at a station system using a wearable electronic device.

In the appended figures, similar components and/or features may have the same numerical reference label. Further, various components of the same type may be distinguished by following the reference label by a dash followed by a second numerical reference label that distinguishes among the similar components and/or features. If only the first numerical reference label is used in the specification, the description is applicable to any one of the similar components and/or features having the same first numerical reference label irrespective of the suffix.

DETAILED DESCRIPTION OF THE INVENTION

Systems, methods, and other techniques are provided in the present disclosure for enabling transit access using electroencephalography (EEG) sensors. Embodiments described herein enable users' thoughts and mental processes to trigger the opening of a transit gate without the use of the users' hands by providing an interface between an EEG sensor and the transit gate. Although the embodiments described herein are directed toward use in transit, it will be understood that embodiments may be utilized in other applications, such as hands-free remote control of cameras, light switch operation, lift controller, raising an alarm or call for help, and the like.

Transit systems traditionally require a user to use his or her hands when accessing transit services, such as entering a subway station, bus, etc. A physical barrier such as a gate is typically opened by requiring some sort of manual interaction from a transit user, such as presenting a ticket, card, phone, etc. But this required interaction can have its drawbacks. For example, it can result in increased time at a gate while the user performs the manual interaction. This is especially true for transit users that may have some physical or other impairment that makes the manual interaction more difficult to perform.

Embodiments described herein address these and other concerns by providing an EEG device for controlling gate operation using, for example, a visual or audible stimulus. More specifically, a specific stimulus (or stimuli) may be located near a transit gate which, when viewed and/or heard by a transit user will form identifiable brain activity in the transit user. When this brain activity is read and identified by a device (e.g., an EEG device incorporated into glasses or some other wearable item) worn by the user, the device can send a wireless message (e.g. via Bluetooth low energy (BLE)) to the gate (when it is determined to be close enough to the gate). The gate can, using local and/or remote resources, identify the user based on the brain activity and/or device identifier, open the gate, and (when needed) charge an account of the user for transit services. Different gates can have different stimuli to ensure the correct gate is opened. Further, the field of vision of the stimuli may be limited to avoid miscalculations (e.g., situating or otherwise showing the stimuli in a way that reduces the likelihood that a user at a first gate might accidentally view the stimuli of a second gate and open the second gate by mistake).

In some embodiments, a transit user having a transit account with the transit system and wearing EEG-enabled glasses can approach a gate in the transit system. Upon viewing visual stimuli associated with that gate, the EEG-enabled glasses may identify brain activity associated with viewing the visual stimuli and transmit a BLE message to the gate. In some embodiments, an application programming interface (API) may be implemented within the glasses/wearable device which can communicate with a gate/station API layer that does the account checking and validation.

An example embodiment may proceed in the following manner. First, glasses (or a similar EEG-enabled device) may identify brain activity associated with a specific visual or auditory stimulus corresponding to a particular transit gate. Second, the glasses may translate the information and send this information (e.g., via a call to an API layer) to a back-end system (which may be a server located in the gate, or a server located remotely), identifying the account ID and gate number. Third, the backend system may check account information and validity to travel. Fourth, the back-end system may send verification information (e.g., a success/error message) to the glasses. Fifth, the glasses may receive the verification information and transmit a BLE message to the gate when it is determined that it is close enough to the gate (e.g., when proximity, as measured by received signal strength indicator (RSSI), is within a certain threshold). Sixth, the gate may verify information in the BLE message (if needed) and then open the gate (e.g., remove a physical barrier), allowing the transit user to pass through. According to some embodiments, some or all messages can be encrypted and decrypted at each end of the communication.

In some embodiments, the back-end system may communicate directly with the gate after receiving information from the glasses, causing the gate to open (without a separate BLE message from the glasses to the gate). In some embodiments, the EEG-enabled device may analyze the brain activity associated with the specific visual stimulus to determine which gate corresponds to the visual stimulus. Embodiments described herein can provide a variety of advantages over traditional transit ticketing. In particular, embodiments herein can provide less able-bodied travelers more independence, reduce time at the gate and corresponding delays, free resources (such as station staff) for other tasks, and/or other such advantages.

FIG. 1 illustrates an example according to the present invention in which a transit user gains entry to a transit system 100 at a station system 110 using a wearable electronic device 150. In some embodiments, wearable electronic device 150 includes one or more EEG sensors that make physical contact with the transit user's head. As the transit user approaches a transit gate 118 (alternatively referred to herein as an access control point 118), the transit user views a visual stimulus 154 displayed by a display system 130 positioned along a side of transit gate 118 that faces the transit user. Viewing visual stimulus 154 causes a particular set of electrical activity in the transit user's brain. Wearable electronic device 150 may then detect an EEG signal related to the electrical activity. In some instances, wearable electronic device 150 may determine the identity of the transit user and the particular gate through which the transit user is attempting to enter transit system 100 based on the EEG signal. This information is wirelessly transmitted to transit gate 118 via a request signal 158, which may cause barriers positioned at transit gate 118 to be removed after verifying that the transit user is permitted to access transit system 100.

Alternatively or additionally, the transit may hear an auditory stimulus 155 outputted by an audio system 120 positioned along a top side of transit gate 118 or along the floor within the passageway formed by transit gate 118. Hearing auditory stimulus 155 may cause a particular set of electrical activity in the transit user's brain, and wearable electronic device 150 may then detect an EEG signal related to the electrical activity. In some embodiments, wearable electronic device 150 may determine that the transit user is currently passing through transit gate 118 based on the EEG signal. This information may be wirelessly transmitted to transit gate 118 via the same or an additional request signal 158, which may allow barriers positioned at transit gate 118 to be removed.

Although wearable electronic device 150 is depicted in FIG. 1 as being attached to the temple of a pair of glasses, wearable electronic device 150 may be implemented in a variety of ways. For example, wearable electronic device 150 may be integrated with the glasses or attached to any part of the glasses, such as the ear piece, the bridge, the rim, the top bar, etc. In some embodiments, wearable electronic device 150 is attached to or integrated with a hat or headband worn by the transit user. In some embodiments, wearable electronic device 150 is directly attached to the transit user using adhesive, suction, or another means of attachment.

Figure 2:
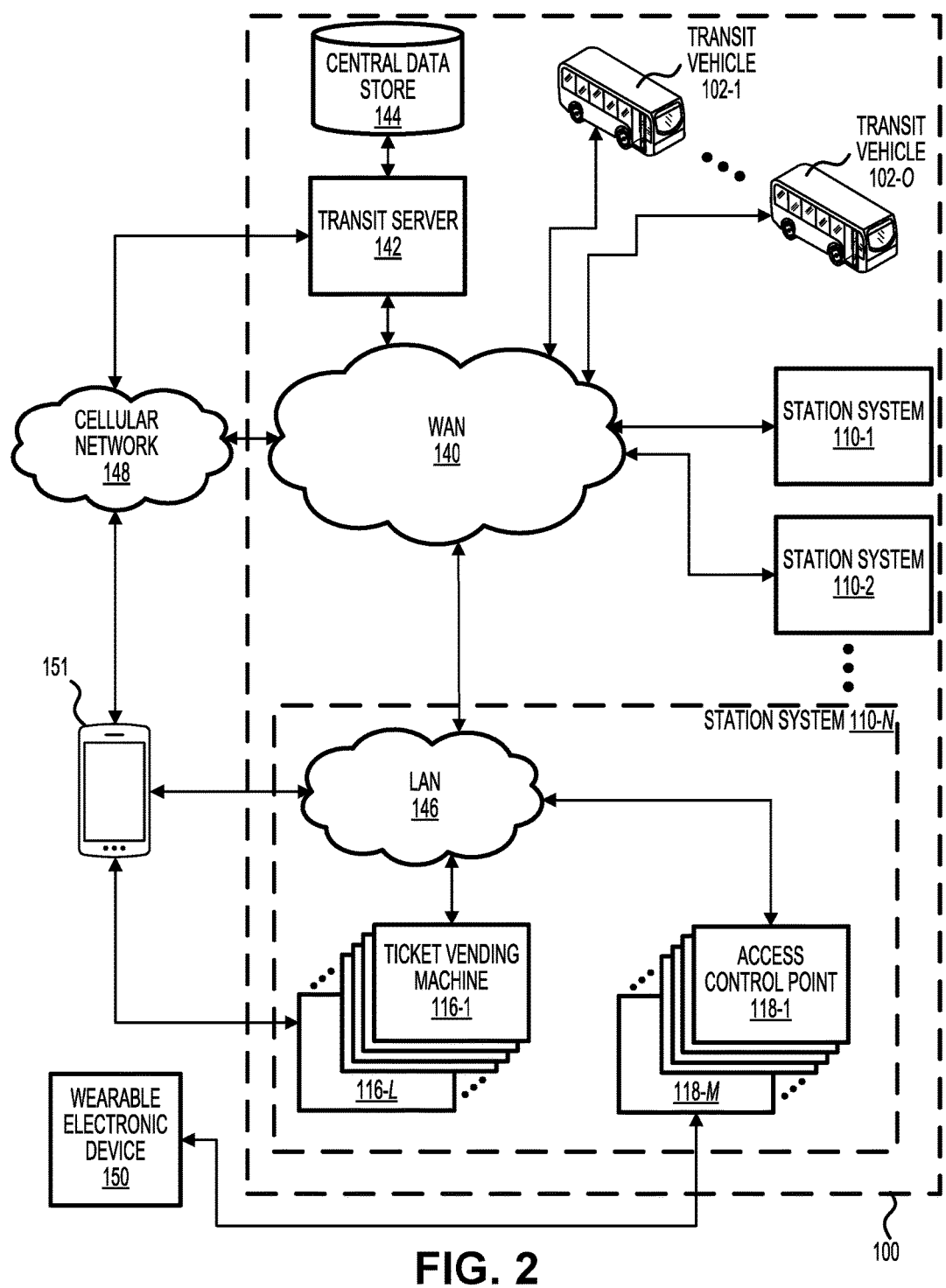
FIG. 2 illustrates a block diagram of a transit system, according to some embodiments of the present invention.

FIG. 2 illustrates a block diagram of transit system 100, according to some embodiments of the present invention. Transit system 100 can include various forms of transit, including subway, bus, ferry, commuter rail, para-transit, etc., or any combination thereof. Transit system 100 may include a plurality of station systems 110 located at a plurality of transit locations (or simply "locations") within transit system 100. While station systems 110 are generally considered to be fixed at transit locations, transit vehicles 102 move along predetermined routes often between different transit locations. For example, a transit user may begin a trip within transit system 100 at one of station systems 110 and may travel within one of transit vehicles 102 to another of station systems 110. Examples of transit vehicles 102 may include a train, a bus, a ferry, a plane, among other possibilities. Transit system 100 achieves interconnectivity between station systems 110, transit vehicles 102, and a transit server 142 via a wide area network (WAN) 140, which may include one or more wired and/or wireless connections. Devices within each of station systems 110 are locally interconnected via a local area network (LAN) 142, which may include one or more wired and/or wireless connections. Data used by transit server 142 in connection with operation of transit system 100 may be stored in a central data store 144 communicatively coupled to transit server 142.

Each of the transit locations may include a non-restricted access area and a restricted access area. The non-restricted access area may include areas that are freely accessible to the general public, whereas the restricted access area may be reserved exclusively for customers of transit system 100. Examples of a restricted access area may include: the inside of transit vehicles 102, a bus or train platform, the inside of a bus or train station, and the like. Each of station systems 110 may include various transit machines such as ticket vending machines 116 and access control points 118. Typically, each of ticket vending machines 116 is configured to allow a transit user to purchase a transit product such as a train or bus ticket and each of access control points 118 corresponds to a location where a transit product is to be presented or is required to be in the transit user's possession. In some embodiments, each of access control points 118 includes an entry point to transit system 100 that defines a passageway and separates the non-restricted access area from the restricted access area. Examples of access control points 118 include a gate, a turnstile, a platform validator, an entrance/exit to transit vehicles 102, among other possibilities. Each of ticket vending machines 116 and access control points 118 may be communicatively coupled to LAN 146 via one or more wired and/or wireless connections.

In some embodiments, transit users may create and maintain a transit user account. The transit user account can comprise information regarding the transit user, such as a name, address, phone number, email address, user identification (such as a unique identifier of the user or other user ID), passcode (such as a password and/or personal identification number (PIN)), an identification code associated with a fare media used to identify a transit user and/or a transit user account, information regarding user preferences and user opt-in or opt-out selections for various services, product(s) associated with the transit user account, a value and/or credit associated with the product(s), information regarding a funding source for the transit user account, among other possibilities. A transit user may request a transit user account and provide the information listed above by phone (such as a call to a customer service center maintained and/or provided by transit system 100), on the Internet, at one of ticket vending machines 116, or by other means. Transit server 142 can use the information provided by the user to create the transit user account, which can be stored and/or maintained on a database, such as central data store 144.

In some embodiments, a funding source can be linked to a transit user account to provide funding to purchase transit products. The funding source can be external to transit system 100 and can be maintained by a financial institution. Such a funding source may include a savings or checking account, a prepaid account, a credit account, an e-commerce account (such as a PAYPAL® account), or more, which can transfer funds via automated clearing house (ACH) or other means. If a transit user account comprises information regarding a funding source, transit server 142 can use the information to fund purchases or other transactions of a transit user. These transactions can be made at station systems 110, transit vehicles 102, on the Internet, by phone, text, email, or a variety of other different ways, and transaction information can then be sent to transit server 142 to update the transit user account associated with the transactions and reconcile payments and purchases with the funding source. The transit server 142 can communicate with the financial institution (or other entity maintaining the funding source) through a financial network (not shown).

A transit user may interact with transit system 100 using a portable electronic device 151 communicatively coupled with various components of transit system 100. Portable electronic device 151 may be a smart phone or other mobile phone (including a near-field-communication (NFC)-enabled mobile phone), a tablet personal computer (PC), a personal digital assistant (PDA), an e-book reader, or other device. A communicative link from portable electronic device 150 to transit server 142 can be provided by a cellular network 148 in communication with WAN 140 or in direct communication with transit server 142. Portable electronic device 151 can thereby access and/or manage information of a transit user account. Furthermore, transit server 142 can send messages to portable electronic device 151 providing transit, account, and/or advertisement information to the transit user in possession of portable electronic device 151. Such messages may be based on, among other things, opt-in or opt-out selections and/or other user preferences as stored in a transit user account. A transit user can use portable electronic device 151 to download a transit application from transit server 142 or from a mobile application source. The mobile application source may be an application store or web site provided by a mobile carrier or the hardware and/or software provider of portable electronic device 151.

Figure 3:
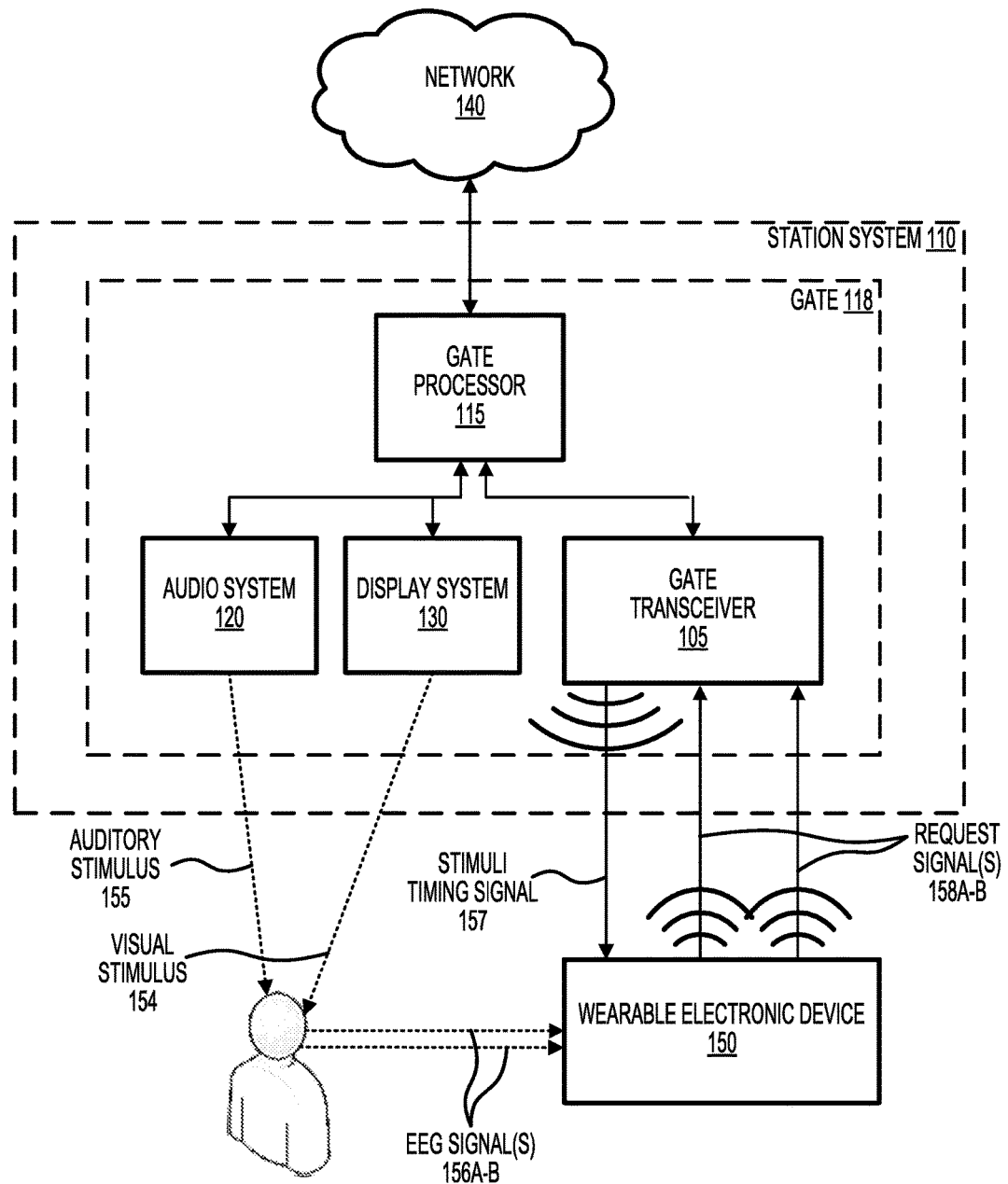
FIG. 3 illustrates a block diagram showing the interaction between various components of a transit system, according to some embodiments of the present invention.

FIG. 3 illustrates a block diagram showing the interaction between various components of transit system 100, according to some embodiments of the present invention. A holder (i.e., wearer) of wearable electronic device 150 may be a transit user of transit system 100 (i.e., customer or a potential customer of transit system 100) and may be inside or outside station system 110 when wearable electronic device 150 communicates with one or more components of transit system 100. For example, the transit user may be inside or outside station system 110 when the transit user views visual stimulus 154 or hears auditory stimulus 155 and an EEG signal 156 is detected by wearable electronic device 150. As another example, wearable electronic device 150 may be inside or outside station system 110 when a request signal 158 is transmitted by wearable electronic device 150 and is received by gate transceiver 105. In some instances, a first EEG signal 156A may be detected as corresponding to electrical activity associated with the transit user viewing visual stimulus 154, and a second EEG signal 156B may be detected as corresponding to electrical activity associated with the transit user hearing auditory stimulus 155. In some instances, a first request signal 158A may be generated and transmitted based on an analysis of first EEG signal 156A, and a second request signal 158B may be generated and transmitted based on an analysis of second EEG signal 156B.

Gate 118 may be used as an entry point into transit system 100 (i.e., a restricted access area of transit system 100) and may, as illustrated in FIG. 1, include a pair of gate cabinets defining a pathway from a non-restricted access area to a restricted access area. One of ordinary skill in the art will recognize that gate 118 can vary in appearance and functionality. Among other possible components, gate 118 may include a gate transceiver 105 for wirelessly communicating with wearable electronic device 150, an audio system 120 for outputting audio stimuli or for giving verbal instructions on using any of the components of gate 118, a display system 130 for displaying visual stimuli 154 or for giving instructions on using any of the components of gate 118, and a gate processor 115 for controlling the functionality of gate 118. One of skill in the art will recognize that barriers associated with gate 118 would open up to allow the holder of wearable electronic device 150 passage upon a successful communication between gate transceiver 105 and wearable electronic device 150.

Gate processor 115 may be in communication with each of gate transceiver 105, audio system 120, display system 130, as well as with network 140. Gate processor 115 may include a single or multiple processors and an associated memory. Gate processor 115 may provide the messaging presented on display system 130. Gate processor 115 may generate the messages to be displayed on display system 130 or receive the message to be displayed from any number of sources over network 140. Gate processor 115 may also generate the messages broadcast from audio system 120 or receive the message to be broadcast from any number of sources over the network 140. Gate processor 115 may communicate with gate transceiver 105 and may determine if the information contained in request signal 158 allows passage or may send the information in request signal 158 over network 140 to transit server 142 to make the determination.

Display system 130 may be any system capable of outputting visual stimulus 154 viewable by the transit user, including a digital display, a projector, a holographic image generator, and the like. Visual stimulus 154 may be generated and outputted by display system 130 or, in other embodiments, may be generated by gate processor 115 and subsequently outputted by display system 130. In some embodiments, display system 130 is configured to output visual stimulus 154 only when it is determined that a transit user is within a threshold distance of gate 118 (e.g., within station system 110). In some embodiments, display system 130 continuously or periodically outputs visual stimulus 154 while gate 118 is powered on.

In addition to outputting/displaying visual stimulus 154, display system 130 may display a message for the transit user that wearable electronic device 150 is not in the correct place and can identify to the holder of wearable electronic device 150 where to correctly place wearable electronic device 150 to allow proper detection of EEG signal 156 and/or proper communication with gate transceiver 105. In other embodiments display system 130 can display any manner of other messages including instructions for using gate 118, instructions for using transit system 100, and advertisements. In some embodiments, gate 118 may include a media reader that requires contact with the object to be read.

In some embodiments, EEG signal 156 is the resulting signal when the electrical activity of the brain is measured or detected by a sensor placed on or near the transit user's head. In some embodiments, wearable electronic device 150 includes one or more electrodes that are physically touching the transit user's head (e.g., scalp). When the transit user views visual stimulus 154 or hears auditory stimulus 155, EEG signal 156 may exhibit certain patterns or characteristics that may be analyzed by wearable electronic device 150 to determine that the transit user is viewing visual stimulus 154 or hearing auditory stimulus 155. In some instances, visual stimulus 154 may change while the transit user is viewing and while the EEG signal 156 is being repeatedly detected by wearable electronic device 150. In such instances, the instant in time that a change is detected in EEG signal 156 may be compared with the instant in time that a change occurred in visual stimulus 154. Similarly, in some instances, auditory stimulus 155 may change while the transit user is hearing auditory stimulus 155 and while the EEG signal 156 is being repeatedly detected by wearable electronic device 150. In such instances, the instant in time that a change is detected in EEG signal 156 may be compared with the instant in time that a change occurred in auditory stimulus 155. In some embodiments, gate transceiver 105 may wirelessly transmit a stimuli timing signal 157 to wearable electronic device 150 that includes timing information for visual stimulus 154 and/or auditory stimulus 155.

Gate transceiver 105 may engage in two-way communication with wearable electronic device 150 or, in some embodiments, gate transceiver 105 may be configured to only receive incoming wireless signals, such as request signal 158. Communication between gate transceiver 105 and wearable electronic device 150 may include any communication technology employing electromagnetic wireless signals. For example, the two devices may communicate using NFC, BLE, radio-frequency identification (RFID), and the like. In some embodiments, gate transceiver 105 may include an RFID reader and wearable electronic device 150 may include an RFID tag. The RFID tag may be passive, active, or battery-assisted passive. Active RFID tags have on-board batteries and periodically or constantly transmit wireless signals with identifying information. Battery-assisted passive RFID tags have small batteries on board and are activated when they are near an RFID reader. Passive RFID tags lack on-board batteries and are instead energized by the wireless signals received from RFID readers. In some embodiments, gate transceiver 105 includes an omni-directional antenna configured to repeatedly transmit stimuli timing signal 157 throughout at least a portion of station system 110.

Figure 4:
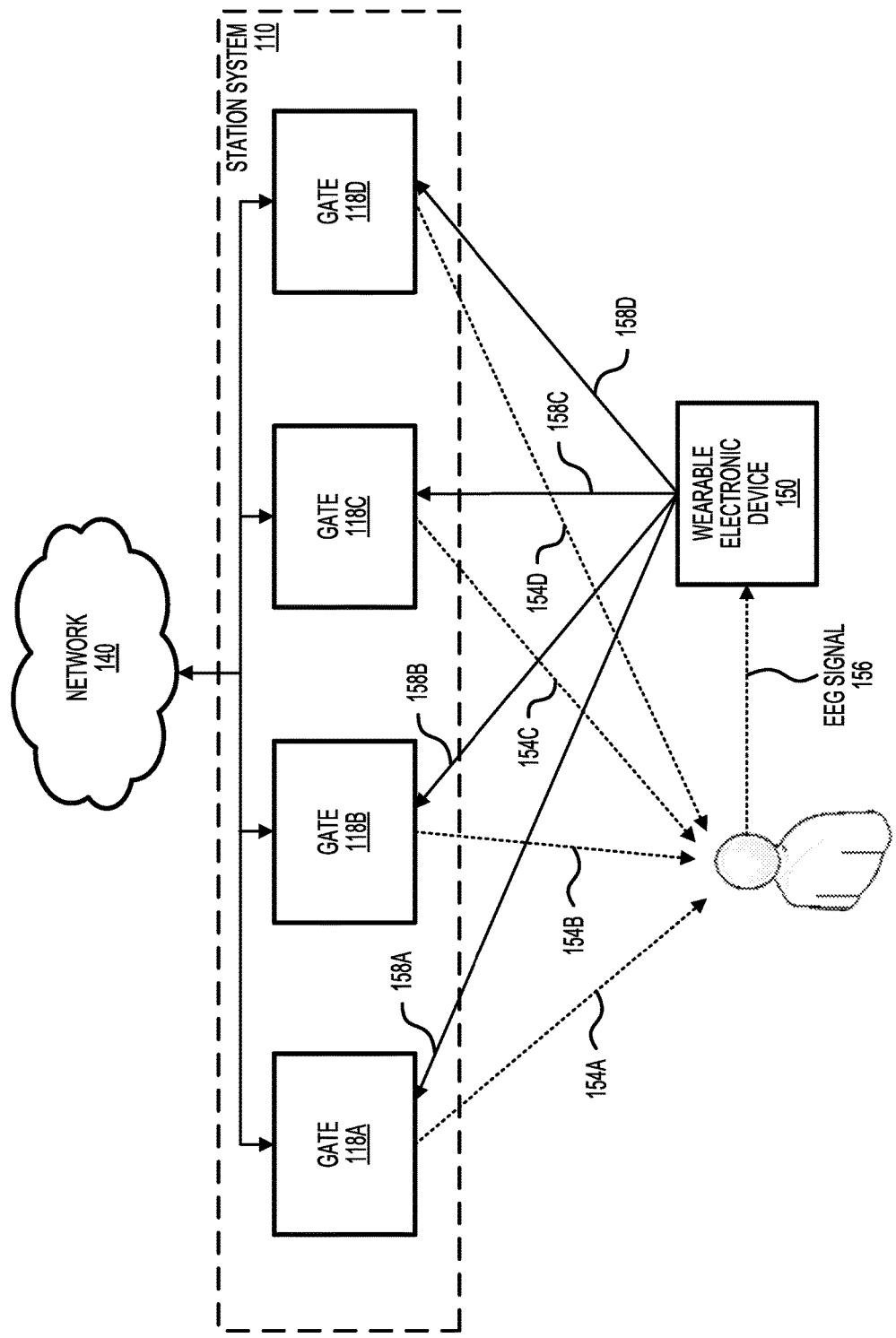
FIG. 4 illustrates a block diagram of a particular embodiment of the present invention in which a station system includes four gates having display systems outputting different visual stimuli.

FIG. 4 illustrates a block diagram of a particular embodiment of the present invention in which station system 110 includes four gates 118 having display systems 130 outputting different visual stimuli 154. For example, visual stimulus 154A may include an identical animation to visual stimulus 154B that is temporally offset by, e.g., 1 or 2 seconds. Alternatively, visual stimulus 154A may include a completely different animation or image than visual stimulus 154B. In some embodiments, display systems 130 are positioned directly on the side of their corresponding gates 118, as illustrated in FIG. 1. In other embodiments, display systems 130 need not be positioned directly on or proximate to gates 118. For example, station system 110 may include a central monitor that displays each of visual stimuli 154 and may provide indicators below each of visual stimuli 154 indicating which gate 118 corresponds to which visual stimulus 154. This allows a first transit user to look at visual stimulus 154A when he/she is walking towards gate 118A and a second transit user to look at visual stimulus 154B when he/she is walking towards gate 118B, etc.

After detecting EEG signal 156, wearable electronic device 150 may analyze EEG signal 156 to determine which of gates 118 the transit user is attempting to enter through. After determining which of gates 118 the transit user is attempting to enter through (i.e., the requested gate), wearable electronic device 150 may send request signal 158 to the requested gate only. Alternatively, or additionally, wearable electronic device 150 may modify request signal 158 to identify the requested gate and may send request signal 158 to each of gates 118. Each of gates 118 may then analyze request signal 158 to determine whether the requested gate is another gate or the current gate. If the requested gate matches the current gate, then the current gate may allow the transit user to access transit system 100 by, for example, opening a gate or turnstile.

Figure 5:
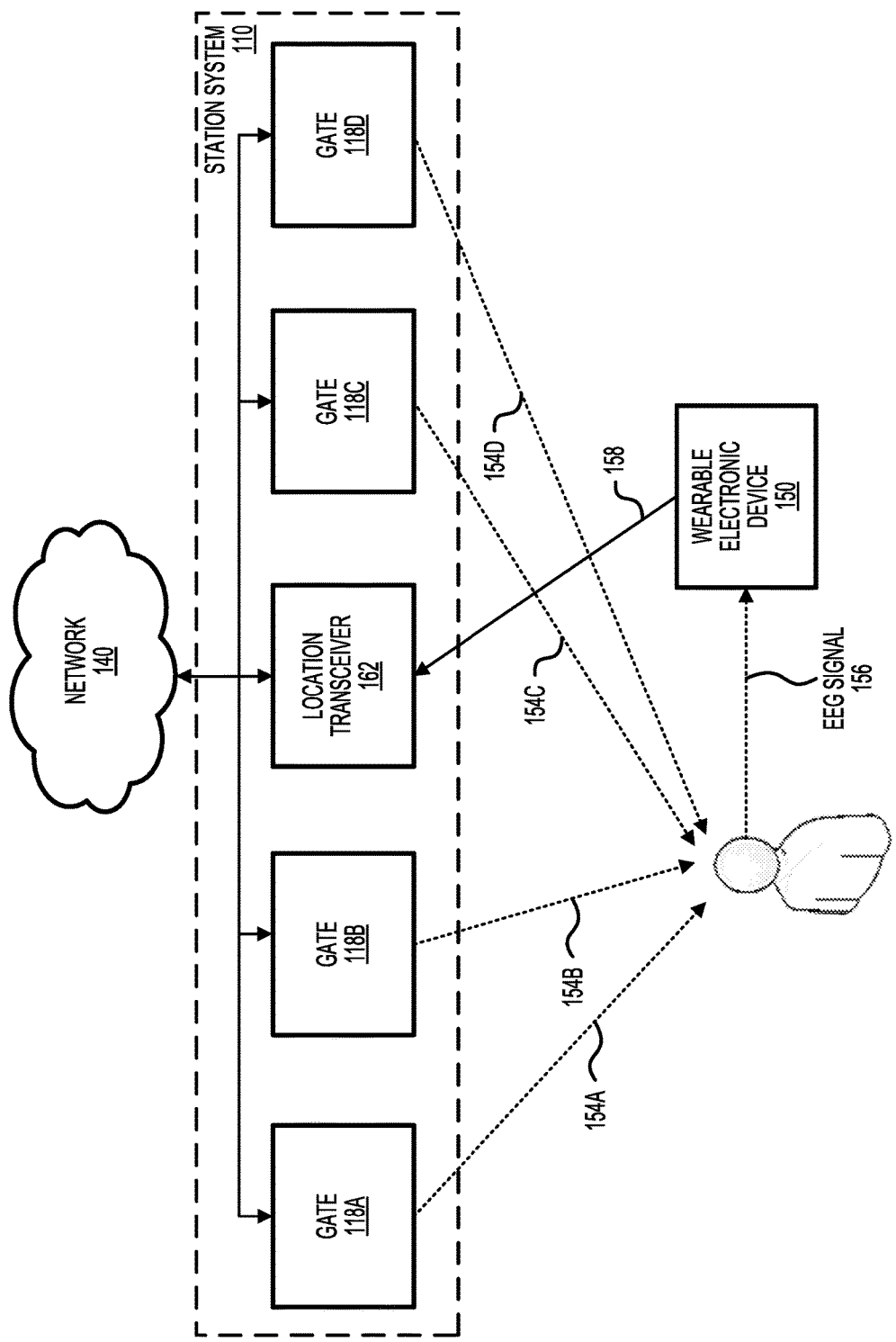
FIG. 5 illustrates a block diagram of an alternative embodiment in which a location transceiver conducts some or all of the wireless communication instead of gate transceivers.

FIG. 5 illustrates a block diagram of an alternative embodiment in which a location transceiver 162 conducts some or all of the wireless communication instead of gate transceivers 105. For example, location transceiver 162 may be configured to transmit stimuli timing signal 157 and receive request signal 158. Location transceiver 154 may be communicatively coupled with each of gates 118 and may be located within station system 110 so as to be in a close proximity to transit users as they approach gates 118. Upon receiving request signal 158 from wearable electronic device 150, location transceiver 162 may analyze request signal 158 to determine which of gates 118 is the requested gate. After identifying the requested gate, location transceiver 162 may forward request signal 158 in its entirety to the requested gate.

Figure 6:
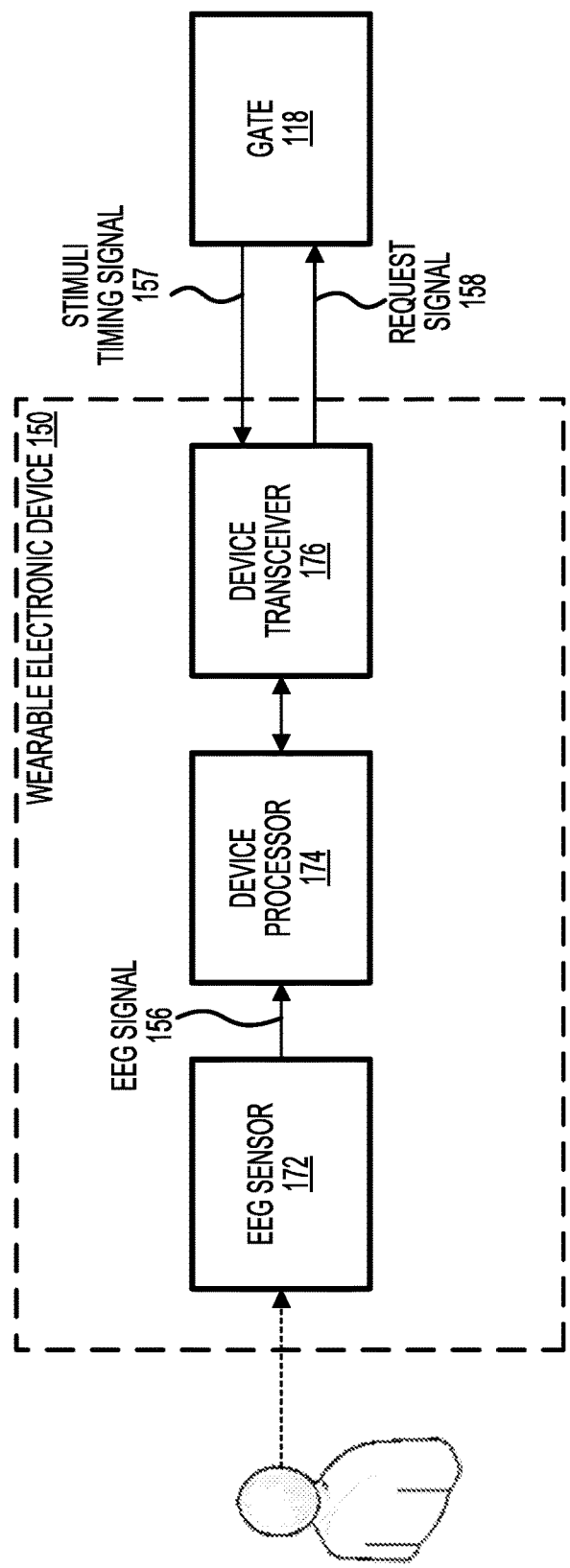
FIG. 6 illustrates a block diagram of a wearable electronic device, according to some embodiments of the present invention.

FIG. 6 illustrates a block diagram of wearable electronic device 150, according to some embodiments of the present invention. Wearable electronic device 150 may include an EEG sensor 172 for detecting EEG signal 156 corresponding to the transit user. EEG sensor 172 may include a voltage sensor and an electrode that may come in physical contact with the transit user's head. EEG sensor 172 may be configured to detect different frequency bands associated with the electrical activity of the transit user's brain, such as the delta band (<4 Hz), the theta band (>4 Hz and <8 Hz), the alpha band (>8 Hz and <14 Hz) and the beta band (>14 Hz). In some embodiments, EEG sensor 172 may be configured to detect only the electrical activity in the beta band as it is related to active thinking. In other embodiments, all frequency bands may be monitored and used for analysis.

Wearable electronic device 150 may include a device processor 174 for receiving and analyzing EEG signal 156 and for generating request signal 158. Device processor 174 may also receive and analyze stimuli timing signal 157, prior to or concurrently with generating request signal 158. Wearable electronic device 150 may include a device transceiver 176 for transmitting and/or receiving wireless signals from gate 118. In some embodiments, device transceiver 176 only includes a transmitter such that stimuli timing signal 157 is not received by wearable electronic device 150. In such embodiments, other characteristics of EEG signal 156 may be analyzed to determine that the transit user is attempting to enter transit system 100 through gate 118, such as a gate-specific and/or a user-specific signature in EEG signal 156.

Figure 7:
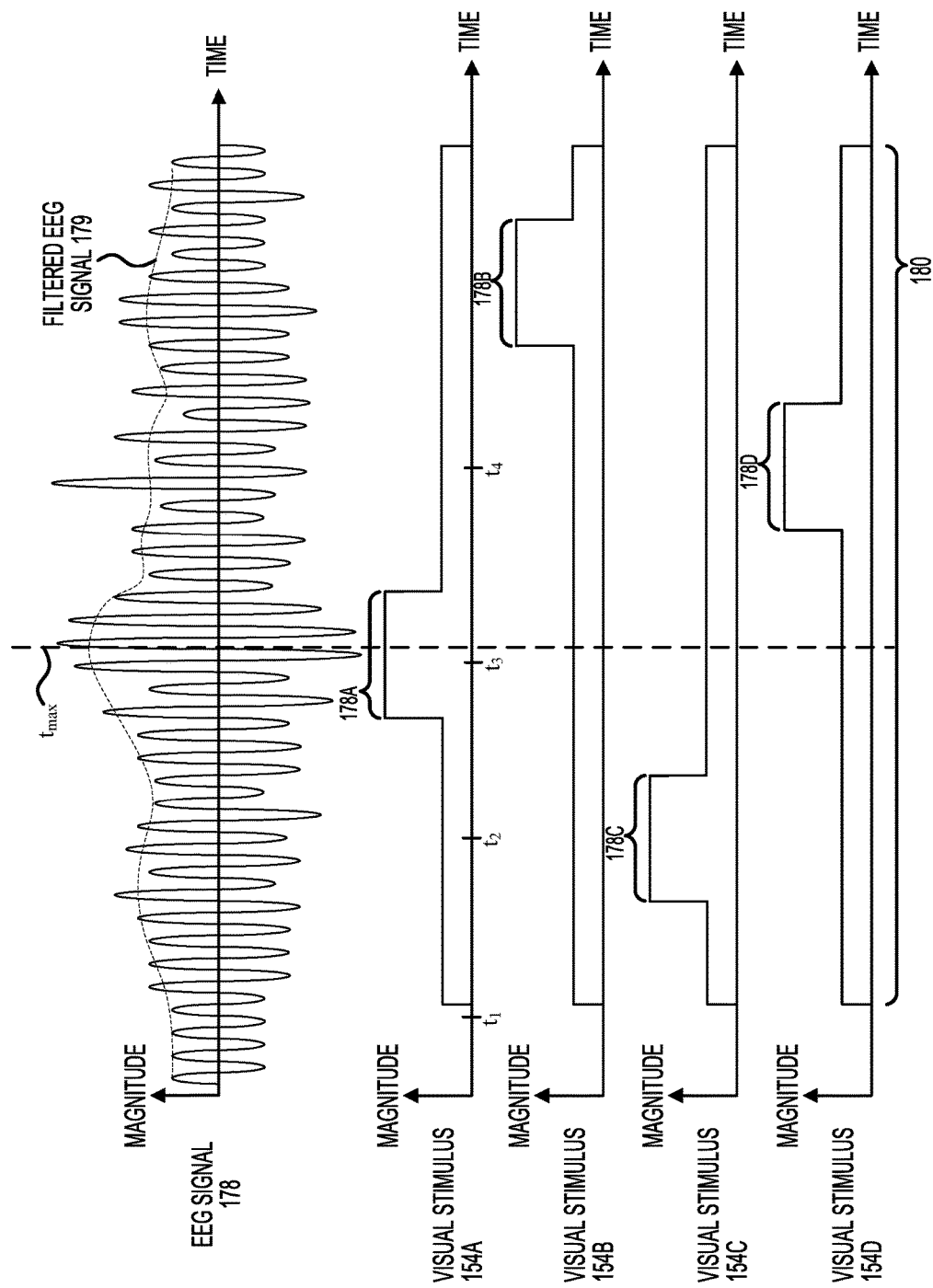

FIG. 7 illustrates an example of the analysis performed by device processor 174 in determining which gate the transit user is attempting to enter transit system 100 through. The magnitude of EEG signal 178 is plotted in the upper portion of FIG. 7 as a function of time. Although EEG signal 178 is shown as having both positive and negative values, in some embodiments EEG signal 178 may be only positive or only negative. Furthermore, EEG signal 178 may also include phase information that is useful for the analysis. As described previously, EEG signal 178 is available to device processor 174 using EEG sensor 172.

In the lower portion of FIG. 7, magnitude signals of visual stimulus 154 are plotted as a function of time. The time axis for each of the plots shown in FIG. 7 may correspond to each other such that comparisons may be made along any vertical line. Magnitude signals of visual stimuli 154 may correspond to various features of the displayed information. For example, the magnitudes of visual stimuli 154 may be proportional to movement, brightness, color, vertical or horizontal placement of the displayed information, etc. In one particular implementation, the magnitudes of visual stimuli 154 are proportional to the speed of a circle moving horizontally across the display such that higher magnitudes correlate with higher velocities of the circle. In another implementation, the magnitudes of visual stimuli 154 are proportional to the brightness of the display such that higher magnitudes correlate with brighter images/animations. In another implementation, the magnitudes of visual stimuli 154 are proportional to the frequency of a blinking light animation such that higher magnitudes correlate with higher blinking frequencies. Other possibilities are contemplated.

The plotted magnitudes of visual stimuli 154 shown in FIG. 7 may be available to device processor 174 through one of two approaches. In the first approach, the information may be contained in stimuli timing signal 157 such that wearable electronic device 150 may receive the information when the transit user approaches station system 110. The advantages of this approach is that only a small amount of information needs to be transmitted wirelessly to reconstruct the magnitude signals due to the simplicity of the signals. For example, the magnitude signal of visual stimulus 154A can be recreated with four time values (time of first step up, time of second step up, time of first step down, and time of second step down) and two magnitude values (magnitude of first step and magnitude of second step). The remaining magnitude signals of visual stimuli 154B, 154C, and 154D may be recreated with even fewer values given their similarity to visual stimulus 154A. In some embodiments, the magnitude signals are defined by time ranges 178 (the time range of the maximum magnitude) and an interrogation time range 180 (the time range of non-zero magnitude). Time ranges 178 may be defined by a single value (starting time, ending time, some arbitrary middle time) when time ranges 178 have a known duration, or by two values (starting time and ending time, or starting time and duration, etc.).

In the second approach, the magnitude signals of visual stimuli 154 may be stored within wearable electronic device 150 and aligned with an internal clock as the transit user approaches station system 110. For example, wearable electronic device 150 may be programmed for a particular transit location or a particular transit system with pre-known visual stimuli 154. As another example, wearable electronic device 150 may include a library of different magnitude signals of visual stimuli 154 that may be selectable by the transit user.

In the example shown in FIG. 7, device processor 174 may determine that the transit user is attempting to enter transit system 100 through gate 118A by performing the following steps. First, device processor 174 filters EEG signal 178 to generate a filtered EEG signal 179, which may, in some embodiments, be a time-averaged version of EEG signal 178 or an envelope containing the oscillating EEG signal. Second, device processor 174 determines a critical time $t_{max}$ at which filtered EEG signal 179 (or EEG signal 178) exhibits a maximum value. Critical time $t_{max}$ has a restraint of being within interrogation time range 180. Third, device processor 174 identifies which of time ranges 178 includes critical time $t_{max}$. If none of time ranges 178 includes critical time $t_{max}$, then the steps are repeated with additional data. Because critical time $t_{max}$ is within time range 178A, device processor 174 determines that transit user is attempting to enter transit system 100 through gate 118A.

Figure 8:
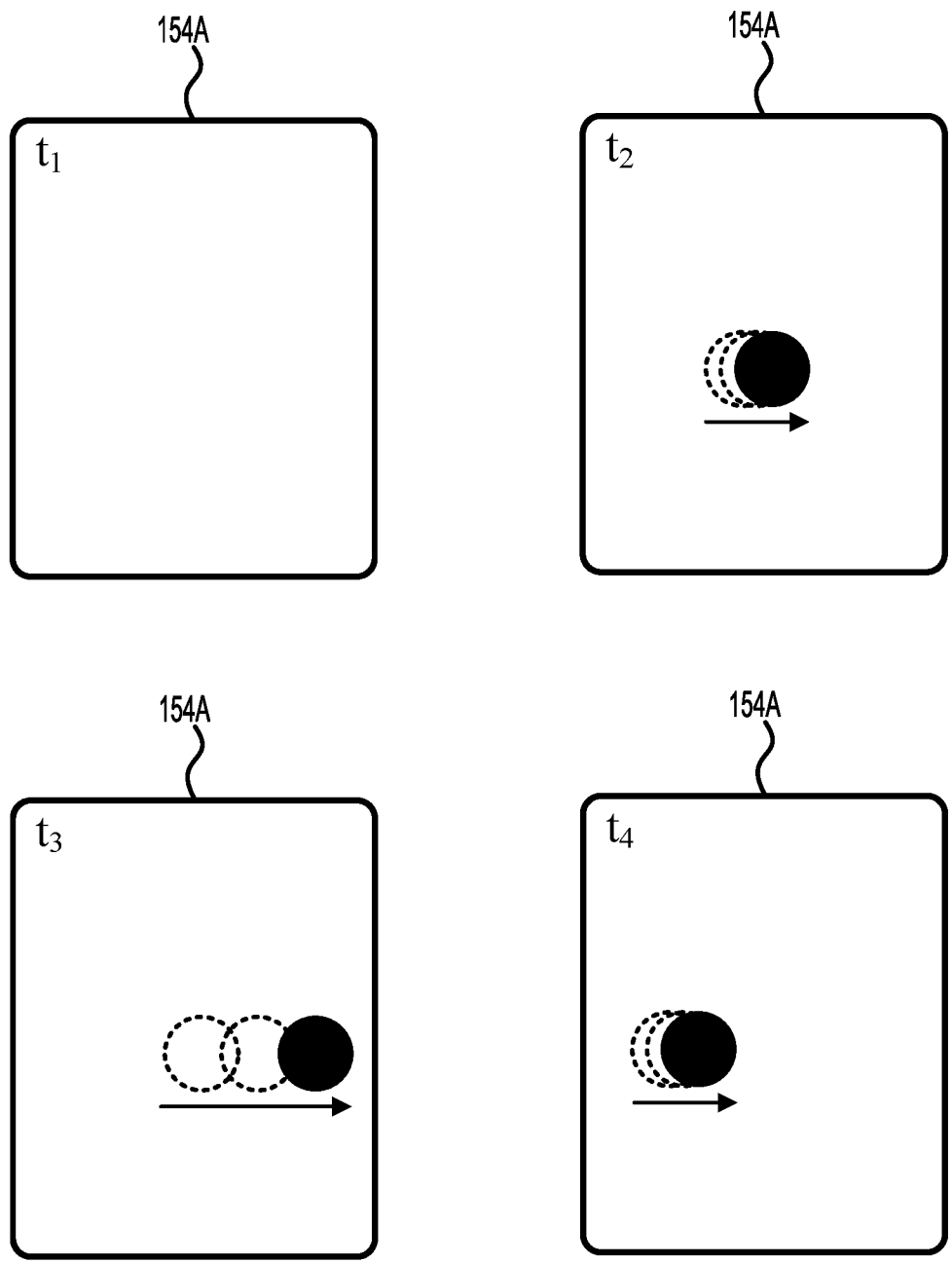
FIG. 8 illustrates four examples of a visual stimulus at four instants in time.

FIG. 8 illustrates four examples of visual stimulus 154A at four instants in time, corresponding to the magnitude signal for visual stimulus 154A shown in FIG. 7. At time $t_1$, visual stimulus 154A is blank and may be set to a default neutral image. At time $t_2$, visual stimulus 154A shows a circle moving horizontally at a low speed. When the circle reaches the right edge of the screen, it wraps around and appears at the left edge of the screen. At time $t_3$, visual stimulus 154A shows the circle moving horizontally at a high speed, the high speed being greater than the low speed. At time $t_4$, visual stimulus 154A shows the circle moving horizontally at the low speed. In this manner, the higher speed of the circle at time $t_3$ may cause the viewer (i.e., the transit user) to exhibit greater brain electrical activity at certain frequency bands than for lower speeds of the circle.

Figure 9:
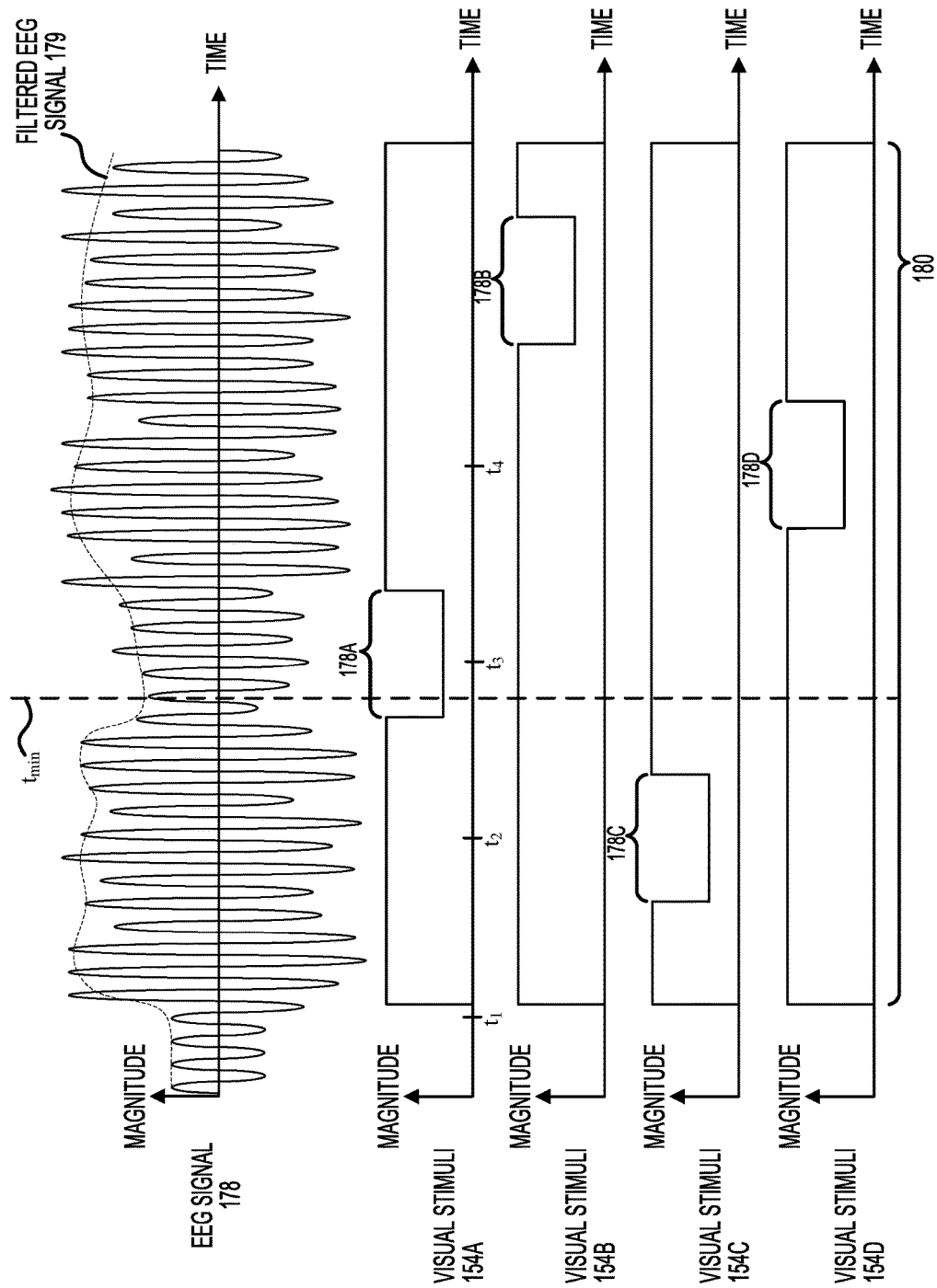

FIG. 9 illustrates an example of the analysis performed by device processor 174 in determining which gate the transit user is attempting to enter transit system 100 through. The magnitude of EEG signal 178 is plotted in the upper portion of FIG. 9 as a function of time, and magnitude signals of visual stimuli 154 are plotted as a function of time in the lower portion of FIG. 9. The time axis for each of the plots shown in FIG. 9 may correspond to each other such that comparisons may be made along any vertical line.

In the example shown in FIG. 9, device processor 174 may determine that the transit user is attempting to enter transit system 100 through gate 118A by performing the following steps. First, device processor 174 filters EEG signal 178 to generate a filtered EEG signal 179. Second, device processor 174 determines a critical time $t_{min}$ at which filtered EEG signal 179 (or EEG signal 178) exhibits a minimum value, critical time $t_{min}$ having a restraint of being within interrogation time range 180. Third, device processor 174 identifies which of time ranges 178 includes critical time $t_{min}$. If none of time ranges 178 includes critical time $t_{min}$, then the steps are repeated with additional data. Because critical time $t_{min}$ is within time range 178A, device processor 174 determines that transit user is attempting to enter transit system 100 through gate 118A.

Figure 10:
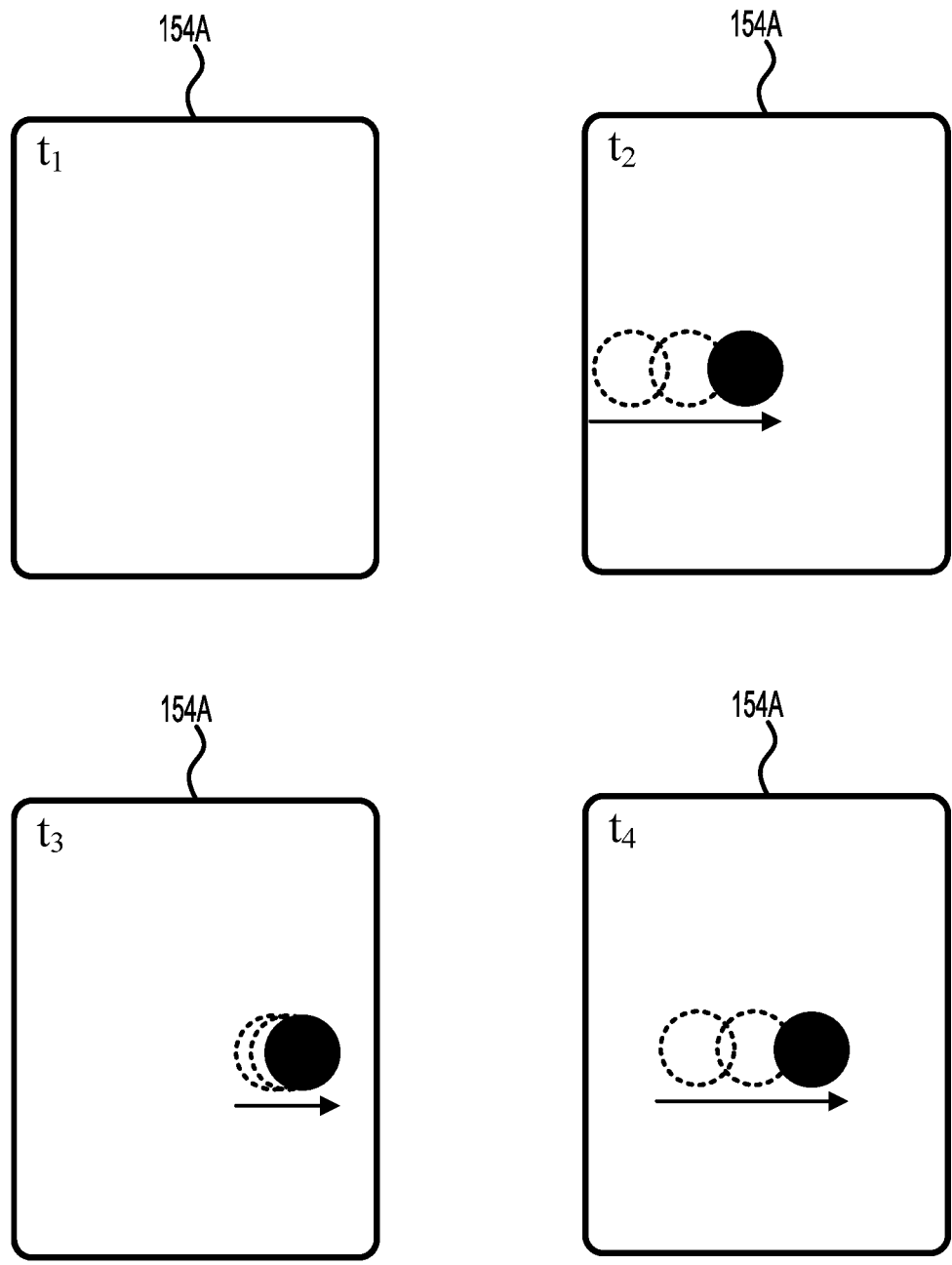
FIG. 10 illustrates four examples of a visual stimulus at four instants in time.

FIG. 10 illustrates four examples of visual stimulus 154A at four instants in time, corresponding to the magnitude signal for visual stimulus 154A shown in FIG. 9. At time $t_1$, visual stimulus 154A is blank and may be set to a default neutral image. At time $t_2$, visual stimulus 154A shows a circle moving horizontally at a high speed. When the circle reaches the right edge of the screen, it wraps around and appears at the left edge of the screen. At time $t_3$, visual stimulus 154A shows the circle moving horizontally at a low speed. At time $t_4$, visual stimulus 154A shows the circle moving horizontally at the high speed. In this manner, the lower speed of the circle at time $t_3$ may cause the viewer (i.e., the transit user) to exhibit lesser brain electrical activity at certain frequency bands than for higher speeds of the circle.

Figure 11:
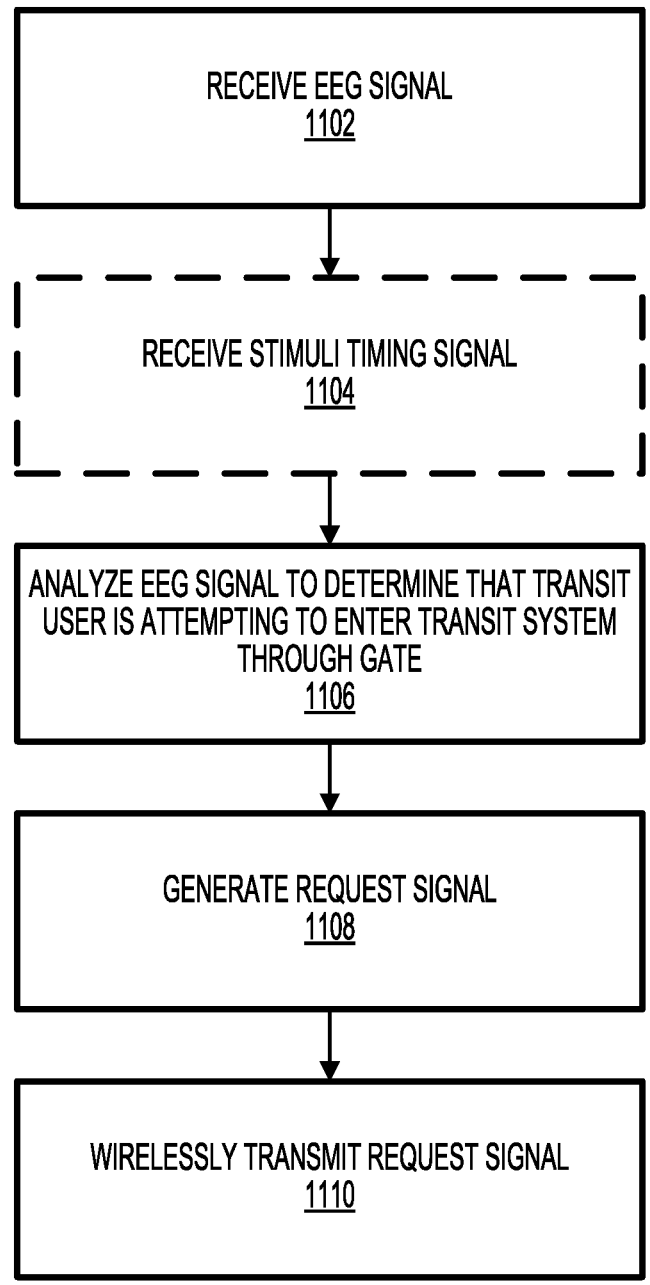
FIG. 11 illustrates a method of using EEG for enabling access to a transit system, according to some embodiments of the present disclosure.

FIG. 11 illustrates a method 1100 of using EEG for enabling access to transit system 100, according to some embodiments of the present disclosure. Steps of method 1100 need not be performed in the order shown, and one or more steps may be omitted during performance of method 1100. In some embodiments, each of the steps of method 1100 are performed by wearable electronic device 150, or some component within wearable electronic device 150 such as device processor 174. In some embodiments, steps of method 1100 are performed by gate 118 in combination with wearable electronic device 150.

At step 1102, EEG signal 156 corresponding to a transit user is received by wearable electronic device 150. In some instances, EEG signal 156 is received by device processor 174 from EEG sensor 172. EEG signal 156 may be detected by EEG sensor 172 using one or more electrodes in physical contact with the transit user's head. In some embodiments, EEG signal 156 is the resulting signal when the electrical activity of the brain is measured or detected by EEG sensor 172. When the transit user is viewing visual stimulus 154, EEG signal 156 may be based at least in part on visual stimulus 154. In some embodiments, EEG signal 156 may be repeatedly received while wearable electronic device 150 is powered on or, in other embodiments or in the same embodiments, EEG signal 156 is received in response to wearable electronic device 150 receiving stimuli timing signal 157 (i.e., step 1102 may be performed in response to performance of step 1104).

At step 1104, stimuli timing signal 157 is received by wearable electronic device 150. In some instances, stimuli timing signal 157 may be wirelessly transmitted from gate transceiver 105 (i.e., gate 118) to device transceiver 176 (i.e., wearable electronic device 150), and may be subsequently routed/sent to device processor 174. Stimuli timing signal 157 may be repeatedly broadcast by gate 118 such that wearable electronic device 150 may determine that the transit user is approaching station system 110 when stimuli timing signal 157 is first received. In some embodiments, stimuli timing signal 157 is transmitted by location transceiver 162 which may be communicatively coupled to a plurality of gates 118.

Stimuli timing signal 157 may include information about visual stimulus 154 that allows wearable electronic device 150 to analyze EEG signal 156 with different analytics than would be possible without the information. In some embodiments, stimuli timing signal 157 includes time range 178 indicating the period of time at which visual stimulus 154 exhibits a decreased magnitude or an increased magnitude. When station system 110 includes multiple gates 118, stimuli timing signal 157 may include multiple time ranges 178 indicating different periods of time at which different visual stimulus 154 exhibit decreased magnitudes or increased magnitudes. Time ranges 178 for different gates 118 may partially overlap or may have no overlap, depending on the embodiment. Stimuli timing signal 157 may also include interrogation time range 180 indicating the period of time at which visual stimulus 154 has a non-zero magnitude.

At step 1106, EEG signal 156 is analyzed by wearable electronic device 150 to determine that the transit user is attempting to enter transit system 100 through a particular gate. In some instances, device processor 174 determines that the transit user is attempting to enter transit system 100 through a particular gate based on EEG signal 156 and stimuli timing signal 157. For example, device processor 174 may determine a critical time at which EEG signal 156 exhibits a minimum magnitude or a maximum magnitude, and may compare the critical time to time ranges 178. If the critical time is within one of time ranges 178, then device processor 174 may determine that the corresponding gate is the particular gate the transit user is attempting to enter through. If the critical time is within none or more than one of time ranges 178, then method 1100 may return to step 1102 to receive a new EEG signal.

In some embodiments, EEG signal 156 may be analyzed to determine whether it contains one or more user characteristics corresponding to the transit user. For example, the transit user may train wearable electronic device 150 by repeatedly viewing visual stimulus 154 while wearable electronic device 150 is in a training mode and is being worn by the transit user. In this manner, wearable electronic device 150 is able to learn and recognize user characteristics within EEG signal 156 over time. Because different transit users may have different user characteristics, wearable electronic device 150 may be transferred and used by different transit users, and wearable electronic device 150 may be able to identify the transit user and determine which visual stimulus 154 the transit user is viewing. Other possibilities are contemplated.

At step 1108, request signal 158 is generated by wearable electronic device 150. In some instances, request signal 158 is generated by device processor 174. Request signal 158 may identify the transit user and may indicate that the transit user is attempting to enter transit system 100 through the particular gate. Accordingly, in some embodiments the only information contained in request signal 158 may be an identifier for the transit user (e.g., name, transit account number) and an identifier for the particular gate (e.g., gate number). In some embodiments, request signal 158 may include EEG signal 156 so that gate 118 may verify (or determine) the identity of the user and the particular gate.

At step 1110, request signal 158 is wirelessly transmitted by wearable electronic device 150 to gate 118. In some instances, request signal 158 is wirelessly transmitted by device transceiver 176 to gate transceiver 105. Alternatively or additionally, request signal 158 may be transmitted by device transceiver 176 to location transceiver 162 and subsequently sent to one or more of gates 118. In response to receiving request signal 158, gate 118 may determine whether the transit user is permitted to access transit system 100 by, for example, determining whether an account balance linked to the transit user has sufficient funds, determining whether the transit user has a transit pass, determining whether the transit user is included in a list of authorized transit users, and the like. In some embodiments, gate 118 may send a communication to transit server 142 to determine whether the transit user is permitted to access transit system 100. Upon determining that the transit user is permitted to enter, gate 118 may cause a barrier to be removed and may display an indication on display system 130 that the transit user is permitted to enter.

Figure 12:
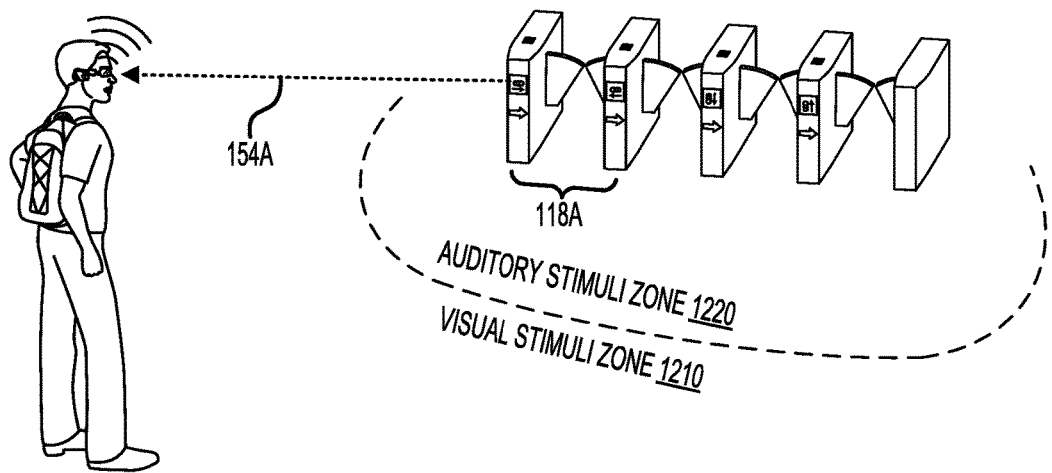
FIGS. 12 and 13 illustrate an example of the present invention in which a transit user approaches a transit gate and passes through a visual stimuli zone and an auditory stimuli zone while entering a transit system.
Figure 13:
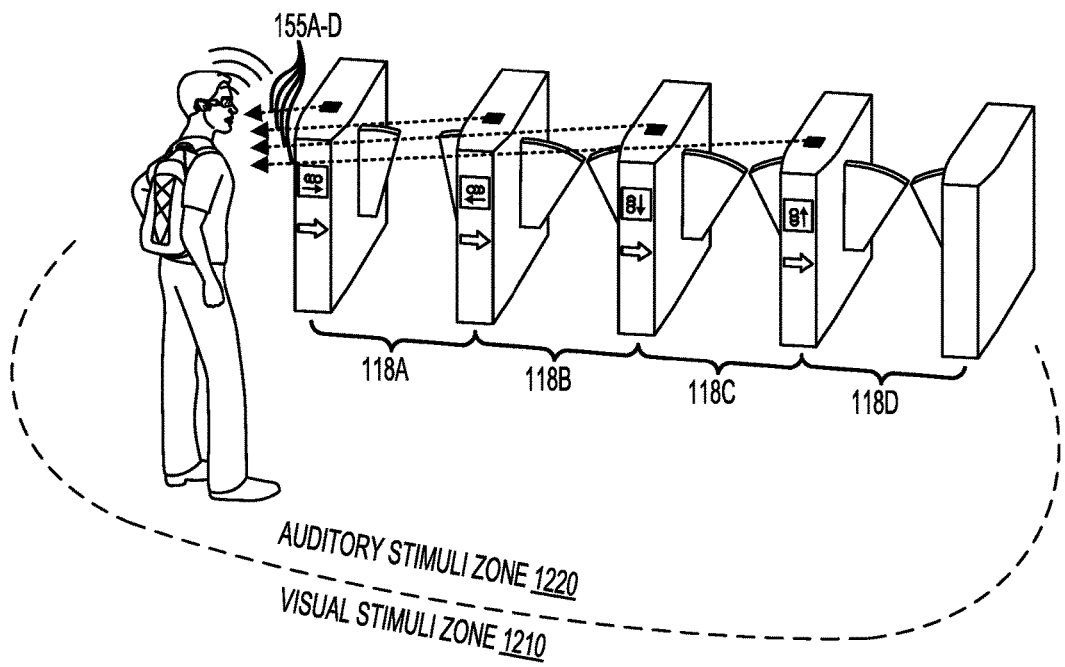

FIGS. 12 and 13 illustrate an example of the present invention in which a transit user approaches transit gate 118 and passes through a visual stimuli zone 1210 and an auditory stimuli zone 1220 while entering transit system 100. In reference to FIG. 12, when the transit user is within visual stimuli zone 1210, the transit user is at a distance from transit gate 118A (e.g., between 10-50 feet) such that he/she is able to view visual stimulus 154A with reasonable clarity such that transit gate 118A can be identified based on analysis of the detected EEG signal corresponding to the transit user viewing visual stimulus 154A. In reference to FIG. 13, when the transit user is within auditory stimuli zone 1220, the transit user is at a distance from transit gate 118A (e.g., less than 10 feet) such that he/she is able to hear auditory stimuli 155 outputted by audio systems of transit gates 118 with reasonable clarity such that it can be determined when the transit user is passing through transit gate 118A based on analysis of the detected EEG signal corresponding to the transit user hearing auditory stimuli 155. In some embodiments, the transit user may hear a single auditory stimulus 155A (outputted by transit gate 118A) or multiple auditory stimuli 155A-D (outputted by transit gates 118A-D). In some embodiments, auditory stimuli zone 1220 includes areas where the transit user is unable to view visual stimulus 154 due to, for example, the position of the display system with respect to the passageway formed by transit gate 118A.

Figure 14:
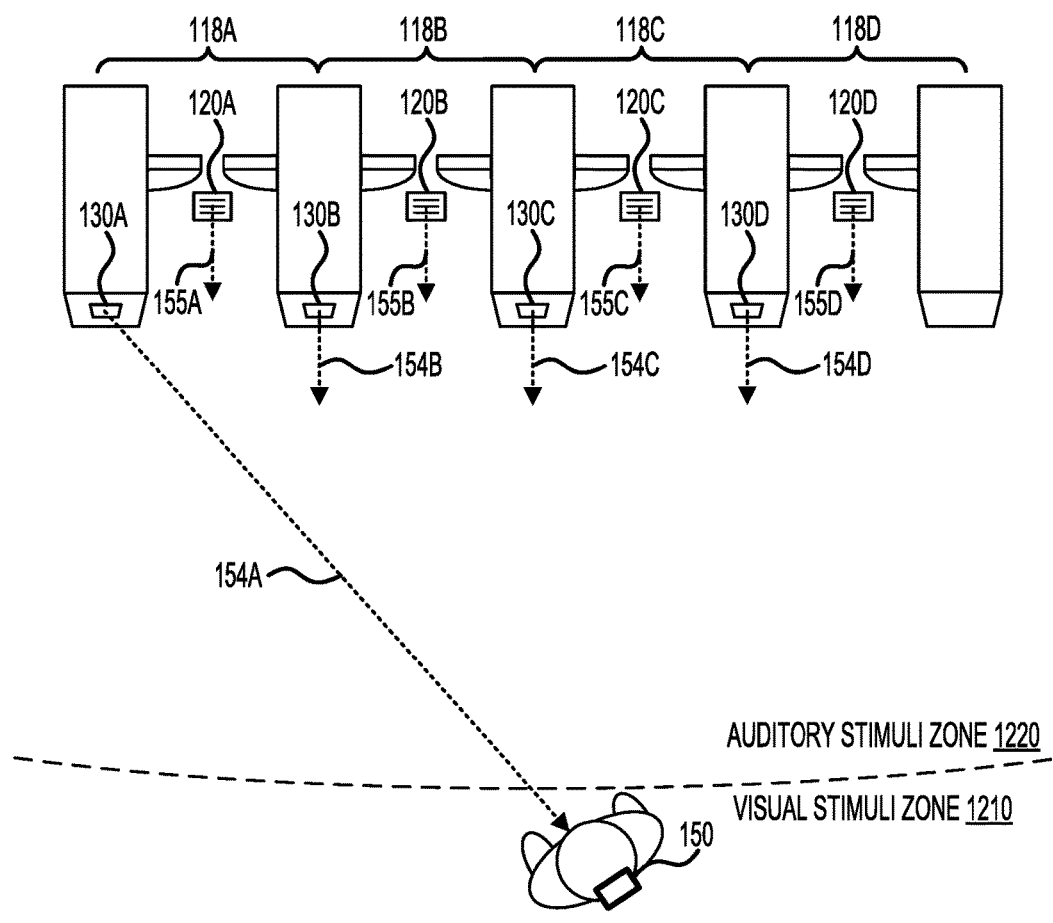
FIGS. 14, 15, and 16 illustrate an example of the present invention in which a transit user approaches a transit gate and passes through a visual stimuli zone and an auditory stimuli zone while entering a transit system.
Figure 15:
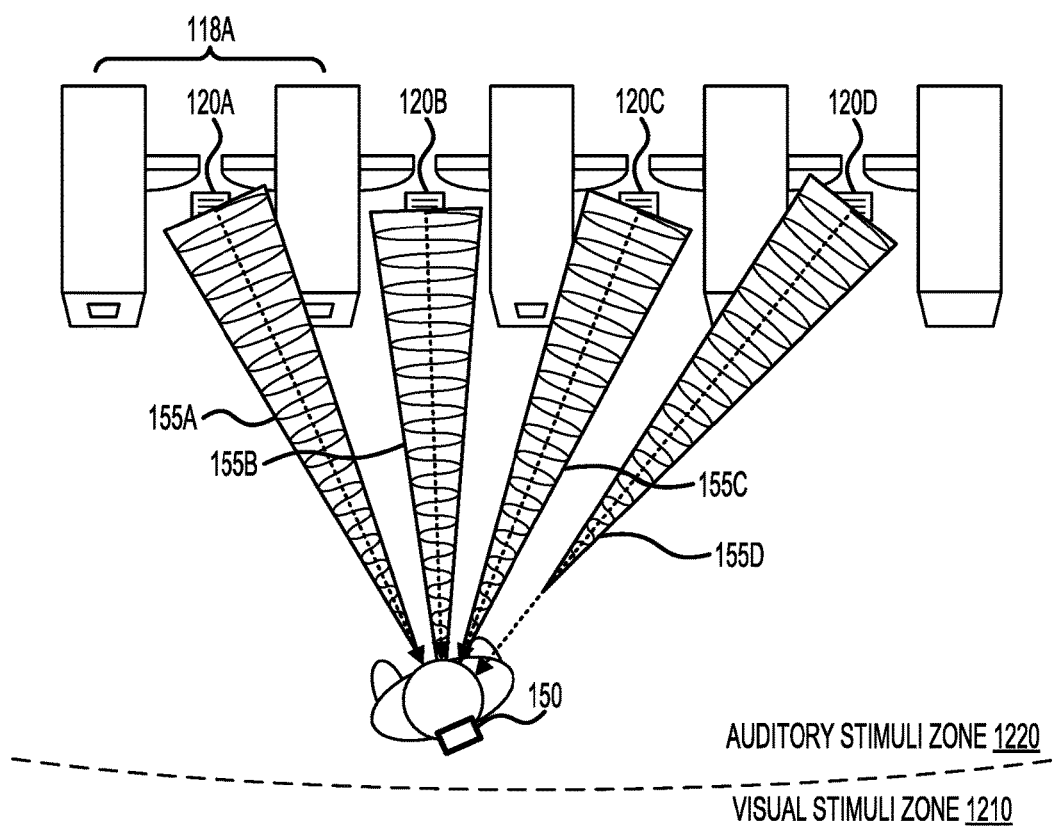
Figure 16:
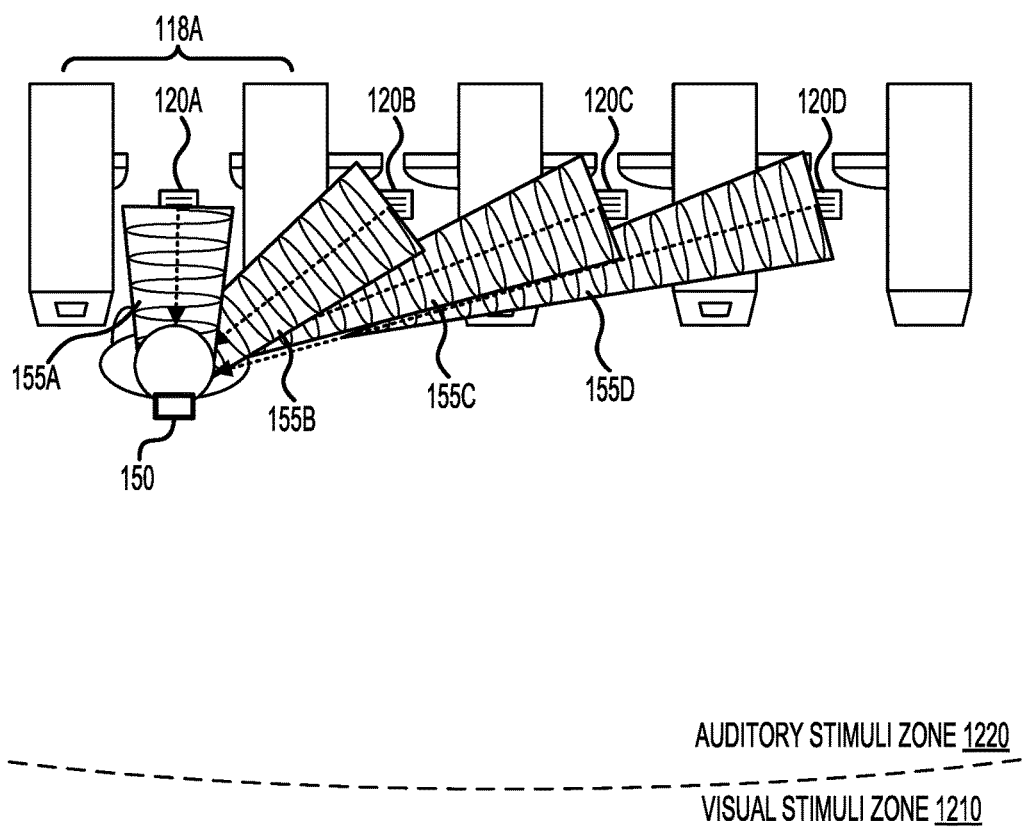

FIGS. 14, 15, and 16 illustrate an example of the present invention in which a transit user approaches transit gate 118A and passes through visual stimuli zone 1210 and auditory stimuli zone 1220 while entering transit system 100. In reference to FIG. 14, the transit user is within visual stimuli zone 1210 when the transit user views visual stimulus 154A being displayed by display system 130A of transit gate 118A. Visual stimuli 154B-D are concurrently being displayed with visual stimulus 154A by display systems 130B-D, respectively. In some embodiments, auditory stimuli 155A-D are concurrently being outputted by audio systems 120A-D, respectively, with visual stimulus 154A being displayed by display system 130A. Due to the distance between the transit user and audio systems 120A-D, the transit user does not hear auditory stimuli 155A-D with reasonable clarity. In some embodiments, audio systems 120A-D initially do not output auditory stimuli 155A-D until receiving request signal 158 from wearable electronic device 150 indicating that the transit user is attempting to enter transit system 100 through transit gate 118A.

In reference to FIG. 15, after the transit user passes from visual stimuli zone 1210 to auditory stimuli zone 1220, the transit user hears auditory stimuli 155A-D being outputted by audio systems 120A-D, respectively. Because the transit user is not yet passing through transit gate 118A, the perceived magnitudes of audio stimuli 155A-D by the transit user are substantially similar and an analysis thereof may indicate that the transit user is not yet passing through transit gate 118A. In some embodiments, audio stimuli 155A-D are outputted sequentially in accordance with a predetermined pattern such that wearable electronic device 150 may distinguish between audio stimuli 155A-D by analyzing EEG signal 156. In other embodiments, or in the same embodiments, each of audio stimuli 155A-D have different frequency components such that wearable electronic device 150 may distinguish between audio stimuli 155A-D by analyzing the EEG signal 156. For example, audio stimulus 155A may be 5 kHz sinusoidal audio signal, audio stimulus 155B may be 7.5 kHz sinusoidal audio signal, audio stimulus 155C may be 10 kHz sinusoidal audio signal, and audio stimulus 155D may be 12.5 kHz sinusoidal audio signal, each of which may be outputted concurrently or sequentially by audio systems 120A-D, respectively.

In reference to FIG. 16, while still within auditory stimuli zone 1220, the transit user continues (or begins) to hear auditory stimuli 155A-D being outputted by audio systems 120A-D, respectively. Because the transit user is passing through transit gate 118A, the perceived magnitudes of audio stimuli 155A-D by the transit user are sufficiently different such that an analysis thereof may indicate that the transit user is passing through transit gate 118A. For example, it may be determined that the transit user is passing through transit gate 118A when it is determined that the perceived magnitude of audio stimulus 155A is greater than the perceived magnitude of audio stimuli 155B-D by at least a threshold amount.

Figure 17:
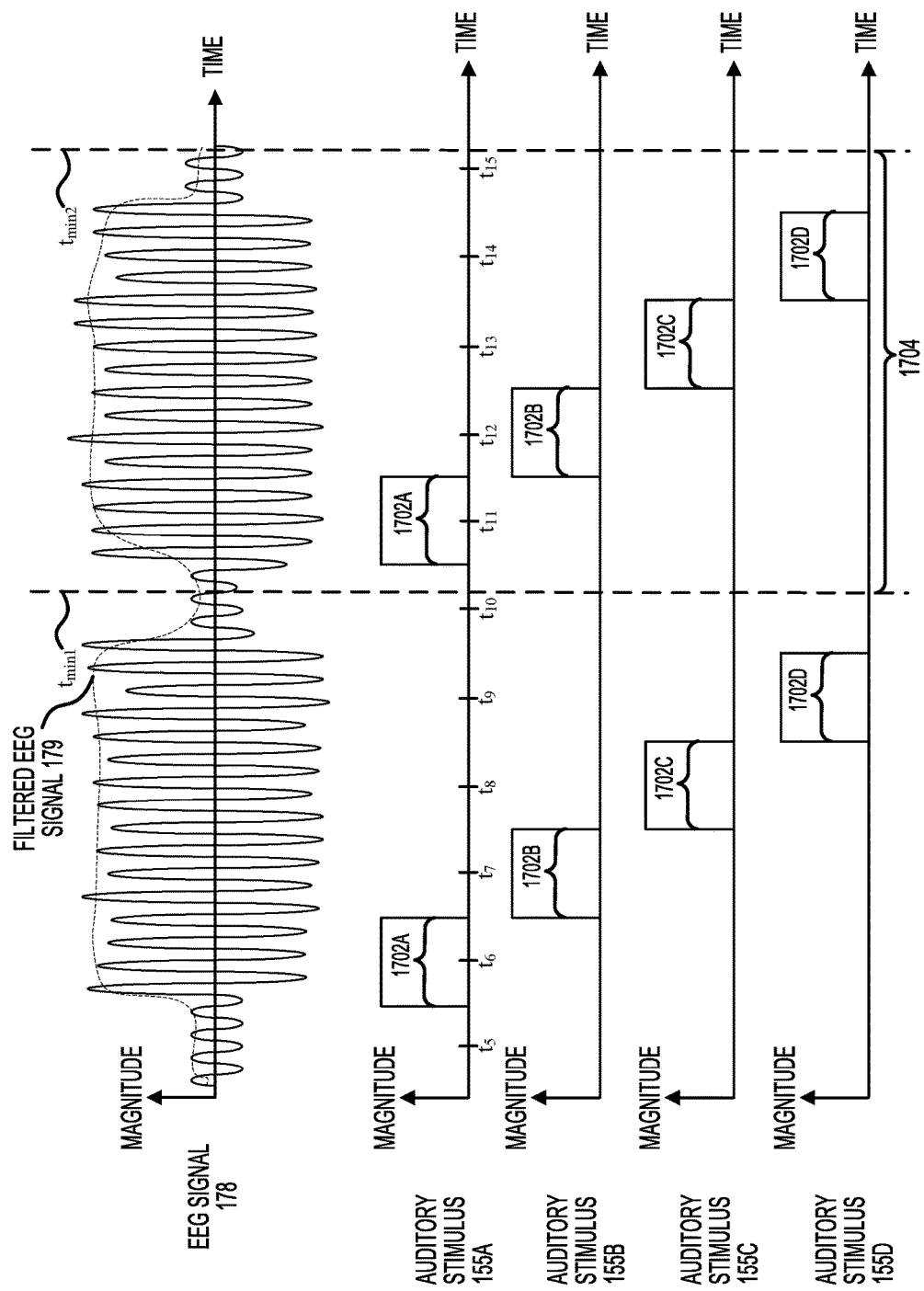
FIG. 17 illustrates an example of the analysis performed by a device processor of a wearable electronic device in determining whether the transit user is passing through a particular transit gate.

FIG. 17 illustrates an example of the analysis performed by device processor 174 of wearable electronic device 150 in determining whether the transit user is passing through a particular transit gate. The plots shown in FIG. 17 correspond to the scene depicted in FIG. 15. The upper portion of FIG. 17 shows the magnitude of EEG signal 178 plotted as a function of time and the lower portion of FIG. 17 shows magnitudes of auditory stimuli 155A-D plotted as a function of time as outputted by audio systems 120A-D, respectively. Although EEG signal 178 is shown as having both positive and negative values, in some embodiments EEG signal 178 may be only positive or only negative. Furthermore, EEG signal 178 may also include phase information that is useful for the analysis. As described previously, EEG signal 178 is available to device processor 174 using EEG sensor 172. The time axis for each of the plots shown in FIG. 17 may correspond to each other such that comparisons may be made along any vertical line. Magnitude signals of auditory stimuli 155 may correspond to various features of the outputted audio signals. For example, the plotted magnitudes of auditory stimuli 155 may be proportional to magnitude, frequency, or phase of the outputted audio signals, etc.

The plotted magnitudes of auditory stimuli 155 shown in FIG. 17 may be determined by device processor 174 through one of several approaches. In one approach, the information may be contained in stimuli timing signal 157 such that wearable electronic device 150 may receive the information when the transit user approaches station system 110. In another approach, the magnitude signals of auditory stimuli 155 may be stored within wearable electronic device 150 and aligned with an internal clock as the transit user approaches station system 110. For example, wearable electronic device 150 may be programmed for a particular transit location or a particular transit system with pre-known auditory stimuli 155. As another example, wearable electronic device 150 may include a library of different magnitude signals of auditory stimuli 155 that may be selectable by the transit user. In another approach, a frame 1704 may be determined by tracking consecutive relative minimum values in filtered EEG signal 179. Frame 1704 may include a repetitive cycle through auditory stimuli 155, and may include short periods of zero audio output which can be easily tracked by device processor 174 to determine frame 1704. In some embodiments, the magnitude signals are defined by time ranges 1702 (the time range of the maximum magnitude) and frame 1704 (the time range of a single cycle).

In the example shown in FIG. 17, device processor 174 may determine that the transit user is not yet passing through gate 118A by performing the following steps. First, device processor 174 filters EEG signal 178 to generate a filtered EEG signal 179, which may, in some embodiments, be a time-averaged version of EEG signal 178 or an envelope containing the oscillating EEG signal. Second, device processor 174 determines a first minimum time $t_{min1}$ at which filtered EEG signal 179 exhibits a relative minimum value. Third, device processor 174 determines a second minimum time $t_{min2}$ at which filtered EEG signal 179 next exhibits a relative minimum value. Fourth, device processor 174 determines frame 1704 based on $t_{min1}$ and $t_{min2}$, and then determines time ranges 1702 based on frame 1704. Fifth, device processor 174 determines whether filtered EEG signal 179 within time frame 1702A is greater than filtered EEG signal 179 within time frames 1702B-D by at least a threshold amount. In the illustrated embodiment, device processor 174 may determine that filtered EEG 179 within time frame 1702 (e.g., at $t_{11}$) is not greater than filtered EEG signal 179 within time frames 1702B-D (e.g., at $t_{12}$, $t_{13}$, or $t_{14}$) by at least the threshold amount, and may therefore determine that the transit user is not yet passing through transit gate 1702A.

Figure 18:
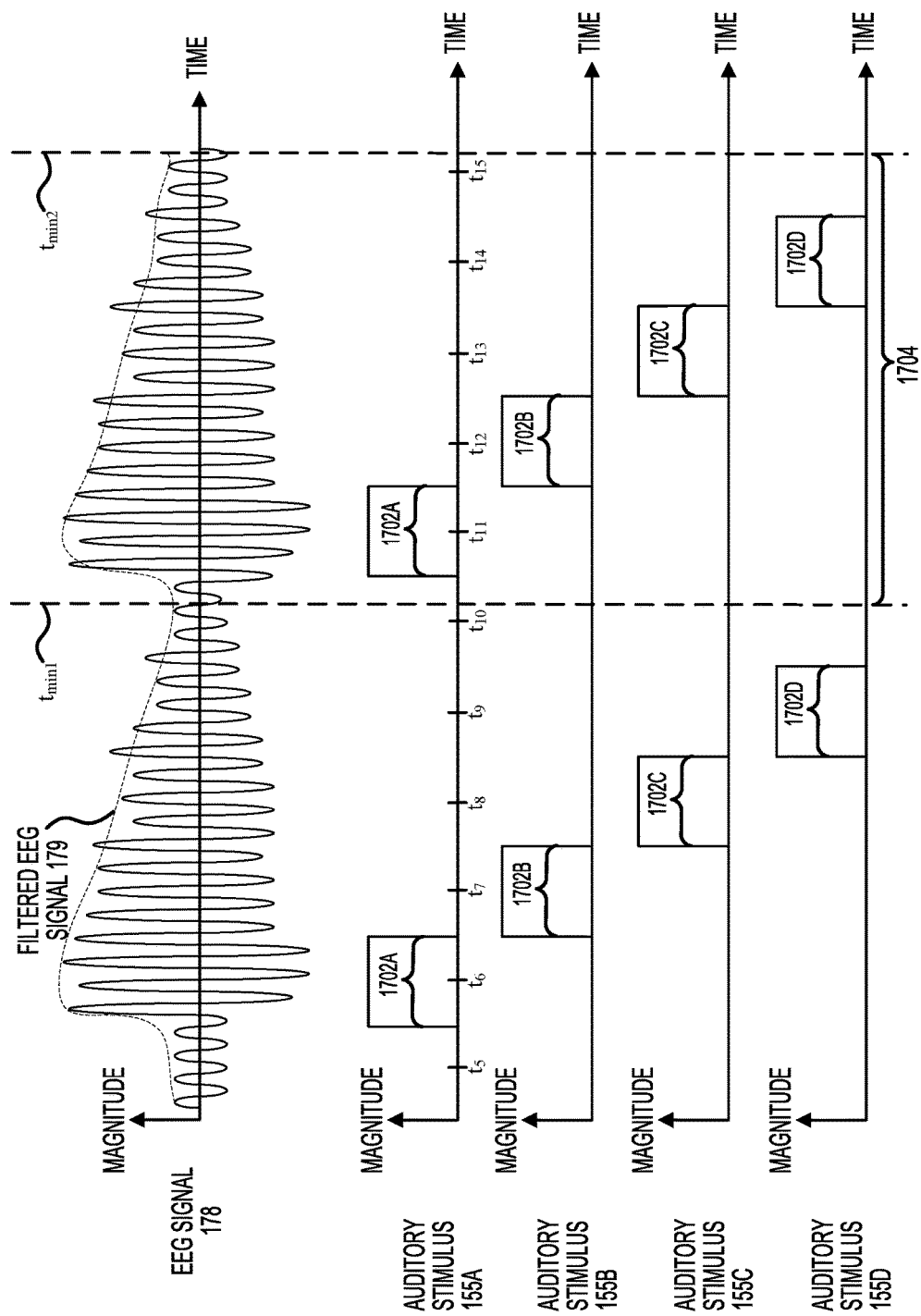
FIG. 18 illustrates an example of the analysis performed by a device processor of a wearable electronic device in determining whether the transit user is passing through a particular transit gate.

FIG. 18 illustrates an example of the analysis performed by device processor 174 of wearable electronic device 150 in determining whether the transit user is passing through a particular transit gate. The plots shown in FIG. 18 correspond to the scene depicted in FIG. 16. The upper portion of FIG. 18 shows the magnitude of EEG signal 178 plotted as a function of time and the lower portion of FIG. 18 shows magnitudes of audio stimuli 155A-D plotted as a function of time as outputted by audio systems 120A-D, respectively. The time axis for each of the plots shown in FIG. 18 may correspond to each other such that comparisons may be made along any vertical line.

In the example shown in FIG. 18, device processor 174 may determine that the transit user is passing through gate 118A by performing the following steps. First, device processor 174 filters EEG signal 178 to generate a filtered EEG signal 179, which may, in some embodiments, be a time-averaged version of EEG signal 178 or an envelope containing the oscillating EEG signal. Second, device processor 174 determines a first minimum time $t_{min1}$ at which filtered EEG signal 179 exhibits a relative minimum value. Third, device processor 174 determines a second minimum time $t_{min2}$ at which filtered EEG signal 179 next exhibits a relative minimum value. Fourth, device processor 174 determines frame 1704 based on $t_{min1}$ and $t_{min2}$, and then determines time ranges 1702 based on frame 1704. Fifth, device processor 174 determines whether filtered EEG signal 179 within time frame 1702A is greater than filtered EEG signal 179 within time frames 1702B-D by at least a threshold amount. In the illustrated embodiment, device processor 174 may determine that filtered EEG 179 within time frame 1702 (e.g., at $t_{11}$) is greater than filtered EEG signal 179 within time frames 1702B-D (e.g., at $t_{12}$, $t_{13}$, or $t_{14}$) by at least the threshold amount, and may therefore determine that the transit user is passing through transit gate 1702A.

Figure 19:
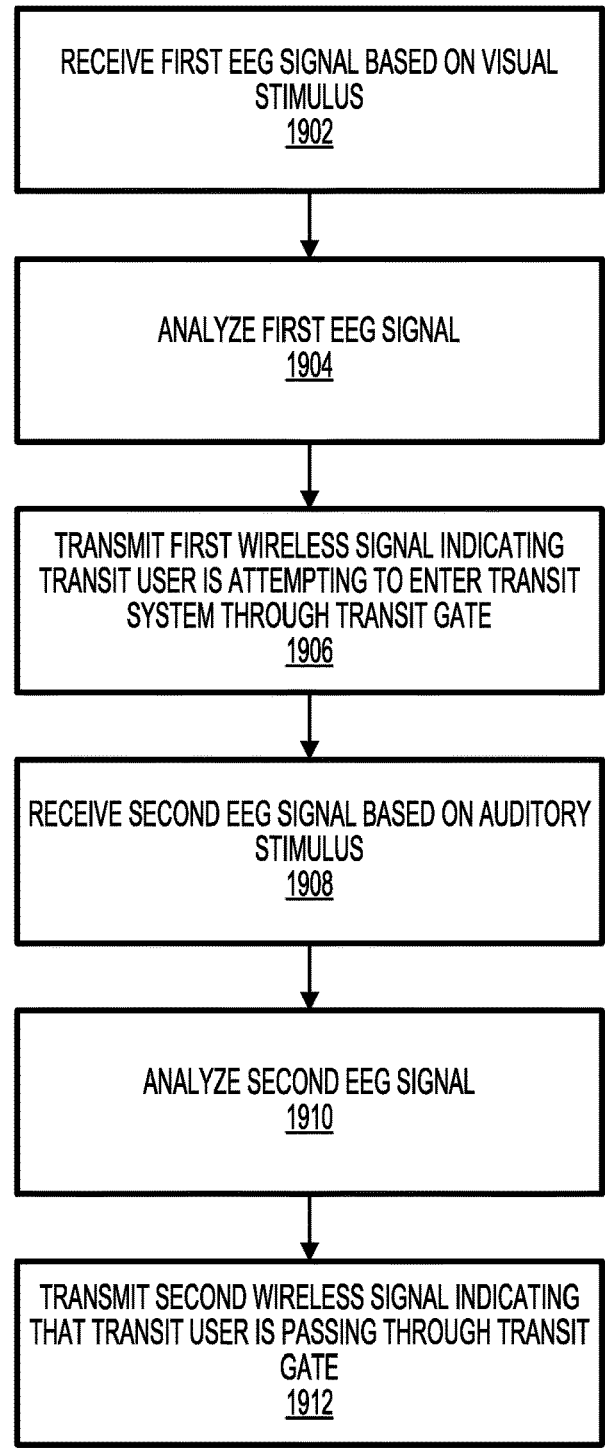
FIG. 19 illustrates a method of using EEG for enabling access to a transit system, according to some embodiments of the present invention.

FIG. 19 illustrates a method 1900 of using EEG for enabling access to transit system 100, according to some embodiments of the present invention. Steps of method 1900 need not be performed in the order shown, and one or more steps may be omitted during performance of method 1900. In some embodiments, each of the steps of method 1900 are performed by wearable electronic device 150, or some component within wearable electronic device 150 such as device processor 174. In some embodiments, one or more steps of method 1900 are performed by transit gate 118.

At step 1902, a first EEG signal 156A is received by wearable electronic device 150. In some instances, first EEG signal 156A is detected by EEG sensor 172 using one or more electrodes in physical contact with the transit user's head, is transmitted by EEG sensor 172 to device processor 174, and is received by device processor 174 from EEG sensor 172. In some embodiments, first EEG signal 156A is the resulting signal when the electrical activity of the transit user's brain is detected by EEG sensor 172 while the transit user is viewing visual stimulus 154. In various embodiments, first EEG signal 156A may be repeatedly received, may be received a single time, may be received in response to transit user causing detection of first EEG signal 156A, and/or may be continuously received while wearable electronic device 150 is powered on.

At step 1904, first EEG signal 156A is analyzed by wearable electronic device 150 to determine that the transit user is attempting to enter transit system 100 through a particular transit gate 118. In some instances, device processor 174 determines that the transit user is attempting to enter transit system 100 through transit gate 118 based on first EEG signal 156A and stimuli timing signal 157. For example, device processor 174 may determine a critical time at which first EEG signal 156A exhibits a minimum magnitude or a maximum magnitude, and may compare the critical time to time ranges 178. If the critical time is within one of time ranges 178, then device processor 174 may determine that the corresponding gate is the particular gate the transit user is attempting to enter through. If the critical time is within none or more than one of time ranges 178, then method 1900 may return to step 1902 to receive a new first EEG signal 156A.

In some embodiments, first EEG signal 156A may be analyzed to determine whether it contains one or more user characteristics corresponding to the transit user. For example, the transit user may train wearable electronic device 150 by repeatedly viewing visual stimulus 154 while wearable electronic device 150 is in a training mode and is being worn by the transit user. In this manner, wearable electronic device 150 is able to learn and recognize user characteristics within first EEG signal 156A over time. Because different transit users may have different user characteristics, wearable electronic device 150 may be transferred and used by different transit users, and wearable electronic device 150 may be able to identify the transit user and determine which visual stimulus 154 the transit user is viewing. Other possibilities are contemplated.

At step 1906, a first wireless signal 158A is generated by wearable electronic device 150 and is transmitted to gate transceiver 105 of transit gate 118 via device transmitter 176. In some instances, first wireless signal 158A is generated and transmitted by device processor 174. First wireless signal 158A may identify the transit user and may indicate that the transit user is attempting to enter transit system 100 through transit gate 118. Accordingly, in some embodiments the only information contained in request signal 158 may be an identifier for the transit user (e.g., name, transit account number) and an identifier for the particular gate (e.g., gate number). In some embodiments, first wireless signal 158A may include first EEG signal 156A so that transit gate 118 may verify (or determine) the identity of the user and the particular gate.

Alternatively or additionally, first wireless signal 158A may be transmitted to location transceiver 162 and subsequently sent to one or more of gates 118. In response to receiving first wireless signal 158A, transit gate 118 may determine whether the transit user is permitted to access transit system 100 by, for example, determining whether an account balance linked to the transit user has sufficient funds, determining whether the transit user has a transit pass, determining whether the transit user is included in a list of authorized transit users, and the like. In some embodiments, transit gate 118 may send a communication to transit server 142 to determine whether the transit user is permitted to access transit system 100. Upon determining that the transit user is permitted to enter, transit gate 118 may cause auditory stimuli 155 to be outputted by audio system 120 and may display an indication on display system 130 that the transit user is permitted to enter.

At step 1908, a second EEG signal 156B is received by wearable electronic device 150. In some instances, second EEG signal 156B is detected by EEG sensor 172 using one or more electrodes in physical contact with the transit user's head, is transmitted by EEG sensor 172 to device processor 174, and is received by device processor 174 from EEG sensor 172. In some embodiments, second EEG signal 156B is the resulting signal when the electrical activity of the transit user's brain is detected by EEG sensor 172 while the transit user is hearing auditory stimulus 155. In various embodiments, second EEG signal 156B may be repeatedly received, may be received a single time, may be received in response to transit user causing detection of second EEG signal 156B, and/or may be continuously received while wearable electronic device 150 is powered on.

At step 1910, second EEG signal 156B is analyzed by wearable electronic device 150 to determine that the transit user is passing through the particular transit gate 118. In some instances, device processor 174 determines that the transit user is passing through transit gate 118 based on second EEG signal 156B and stimuli timing signal 157. For example, device processor 174 may determine frame 1704 and/or time ranges 1702 at which different auditory stimuli 155 exhibit maximum magnitudes, and may be compare the times at which second EEG signal 156B exhibits a maximum magnitude to time ranges 1702.

At step 1912, a second wireless signal 158B is generated by wearable electronic device 150 and is transmitted to gate transceiver 105 of transit gate 118 via device transmitter 176. In some instances, second wireless signal 158B is generated and transmitted by device processor 174. Second wireless signal 158B may indicate that the transit user is passing through transit gate 118. In some embodiments, second wireless signal 158B may indicate that the transit user is currently within the passageway formed by transit gate 118. In some embodiments, second wireless signal 158B may indicate a current location of the transit user and/or a distance or amount of time until the transit user reaches a physical barrier associated with transit gate 118. Accordingly, transit gate 118 may remove the physical barrier associated with transit gate 118 as the transit user reaches the physical barrier such that the transit user may completely pass through transit gate 118 and enter transit system 100 without adjusting his/her speed.

Figure 20:
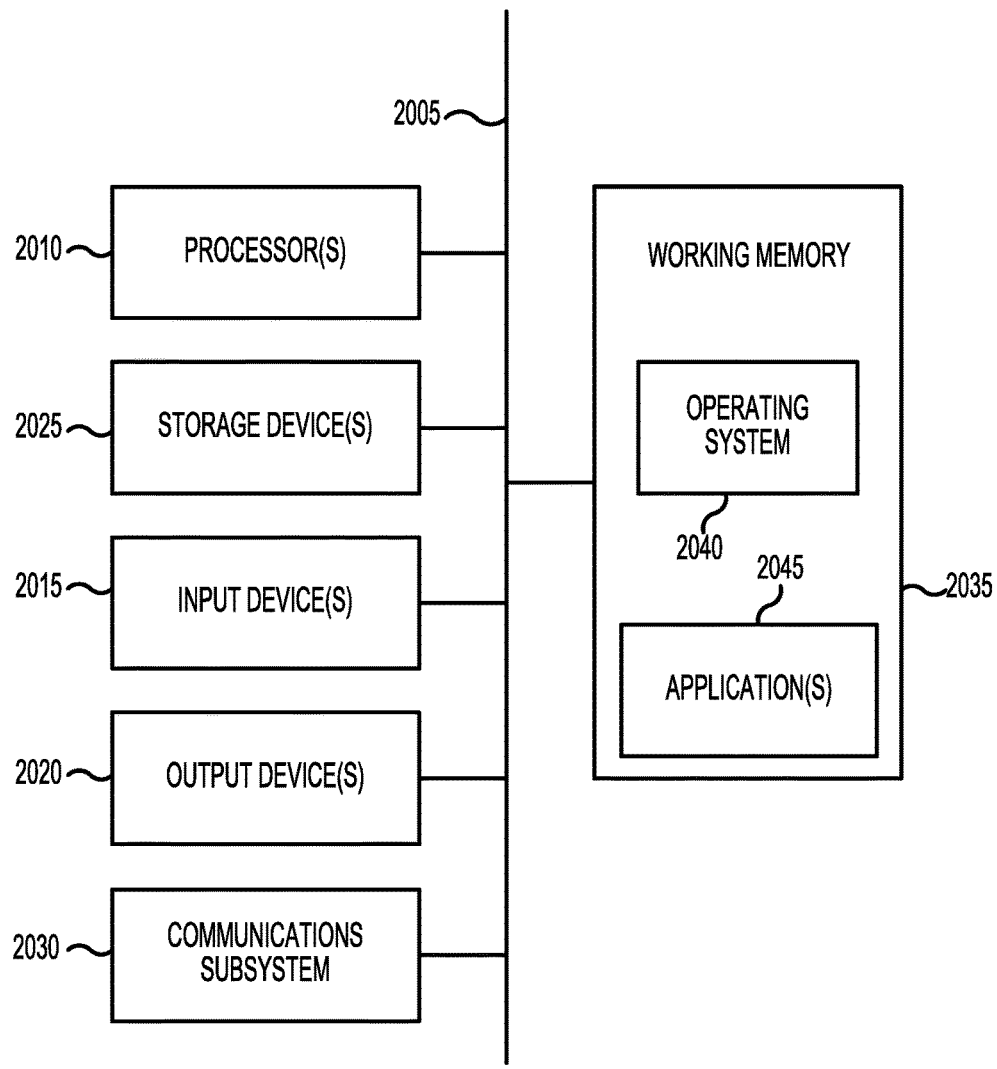
FIG. 20 illustrates a simplified computer system, according to some embodiments of the present disclosure.

FIG. 20 illustrates a simplified computer system 2000, according to some embodiments of the present disclosure. Computer system 2000 as illustrated in FIG. 20 may be incorporated into devices such as wearable electronic device 150 (e.g., EEG sensor 172, device processor 174, device transceiver 176), transit gate 118 (e.g., gate transceiver 105, audio system 200, display system 130, gate processor 115), and transit server 142 as described herein. FIG. 20 provides a schematic illustration of one embodiment of computer system 2000 that can perform some or all of the steps of the methods provided by various embodiments. It should be noted that FIG. 20 is meant only to provide a generalized illustration of various components, any or all of which may be utilized as appropriate. FIG. 20, therefore, broadly illustrates how individual system elements may be implemented in a relatively separated or relatively more integrated manner.

Computer system 2000 is shown comprising hardware elements that can be electrically coupled via a bus 2005, or may otherwise be in communication, as appropriate. The hardware elements may include one or more processors 2010, including without limitation one or more general-purpose processors and/or one or more special-purpose processors such as digital signal processing chips, graphics acceleration processors, and/or the like; one or more input devices 2015, which can include without limitation a mouse, a keyboard, a camera, and/or the like; and one or more output devices 2020, which can include without limitation a display device, a printer, and/or the like.

Computer system 2000 may further include and/or be in communication with one or more non-transitory storage devices 2025, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

Computer system 2000 might also include a communications subsystem 2030, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 2030 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 2030. In other embodiments, a portable electronic device, e.g. the first electronic device, may be incorporated into computer system 2000, e.g., an electronic device as an input device 2015. In some embodiments, computer system 2000 will further comprise a working memory 2035, which can include a RAM or ROM device, as described above.

Computer system 2000 also can include software elements, shown as being currently located within the working memory 2035, including an operating system 2040, device drivers, executable libraries, and/or other code, such as one or more application programs 2045, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 20, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 2025 described above. In some cases, the storage medium might be incorporated within a computer system, such as computer system 2000. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by computer system 2000 and/or might take the form of source and/or installable code, which, upon compilation and/or installation on computer system 2000 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as computer system 2000 to perform methods in accordance with various embodiments of the technology. According to a set of embodiments, some or all of the procedures of such methods are performed by computer system 2000 in response to processor 2010 executing one or more sequences of one or more instructions, which might be incorporated into the operating system 2040 and/or other code, such as an application program 2045, contained in the working memory 2035. Such instructions may be read into the working memory 2035 from another computer-readable medium, such as one or more of the storage device(s) 2025. Merely by way of example, execution of the sequences of instructions contained in the working memory 2035 might cause the processor(s) 2010 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using computer system 2000, various computer-readable media might be involved in providing instructions/code to processor(s) 2010 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 2025. Volatile media include, without limitation, dynamic memory, such as the working memory 2035.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 2010 for execution. Merely by way of example, the instructions may initially be carried on a magnetic disk and/or optical disc of a remote computer. A remote computer might load the instructions into its dynamic memory and send the instructions as signals over a transmission medium to be received and/or executed by computer system 2000.

The communications subsystem 2030 and/or components thereof generally will receive signals, and the bus 2005 then might carry the signals and/or the data, instructions, etc. carried by the signals to the working memory 2035, from which the processor(s) 2010 retrieves and executes the instructions. The instructions received by the working memory 2035 may optionally be stored on a non-transitory storage device 2025 either before or after execution by the processor(s) 2010.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A wearable electronic device for enabling access to a transit system, the wearable electronic device comprising:
   an electroencephalography (EEG) sensor configured to detect EEG signals corresponding to a transit user;
   a device transmitter configured to transmit wireless signals to a gate receiver of a transit gate; and
   a device processor configured to perform operations comprising:
   receiving, from the EEG sensor, a first EEG signal based at least in part on the transit user viewing a visual stimulus associated with the transit gate;
   analyzing the first EEG signal to determine that the transit user is attempting to enter the transit system through the transit gate;
   transmitting, to the gate receiver via the device transmitter, a first wireless signal indicating that the transit user is attempting to enter the transit system through the transit gate;
   receiving, from the EEG sensor, a second EEG signal based at least in part on the transit user hearing an auditory stimulus associated with the transit gate;
   analyzing the second EEG signal to determine that the transit user is passing through the transit gate; and
   transmitting, to the gate receiver via the device transmitter, a second wireless signal indicating that the transit user is passing through the transit gate.

2. The wearable electronic device of claim 1, wherein the transit gate is configured to allow the transit user to enter the transit system in response to receiving the second wireless signal by removing a physical barrier associated with the transit gate.

3. The wearable electronic device of claim 1, wherein the first wireless signal is transmitted concurrently with the second wireless signal.

4. The wearable electronic device of claim 1, wherein the visual stimulus is displayed via a display system located at the transit gate.

5. The wearable electronic device of claim 1, wherein the auditory stimulus is outputted via an audio system located at the transit gate.

6. The wearable electronic device of claim 5, wherein the transit gate is configured to output the auditory stimulus via the audio system in response to receiving the first wireless signal.

7. The wearable electronic device of claim 1, wherein the operations further comprise:
   receiving a stimuli timing signal containing timing information corresponding to one or both of the visual stimulus and the auditory stimulus.

8. A method of enabling access to a transit system, the method comprising:
   receiving, from an electroencephalography (EEG) sensor, a first EEG signal based at least in part on a transit user viewing a visual stimulus associated with a transit gate;
   analyzing the first EEG signal to determine that the transit user is attempting to enter the transit system through the transit gate;
   transmitting a first wireless signal indicating that the transit user is attempting to enter the transit system through the transit gate;
   receiving, from the EEG sensor, a second EEG signal based at least in part on the transit user hearing an auditory stimulus associated with the transit gate;
   analyzing the second EEG signal to determine that the transit user is passing through the transit gate; and
   transmitting a second wireless signal indicating that the transit user is passing through the transit gate.

9. The method of claim 8, wherein the transit gate is configured to allow the transit user to enter the transit system in response to receiving the second wireless signal by removing a physical barrier associated with the transit gate.

10. The method of claim 8, wherein the first wireless signal is transmitted concurrently with the second wireless signal.

11. The method of claim 8, wherein the visual stimulus is displayed via a display system located at the transit gate.

12. The method of claim 8, wherein the auditory stimulus is outputted via an audio system located at the transit gate.

13. The method of claim 12, wherein the transit gate is configured to output the auditory stimulus via the audio system in response to receiving the first wireless signal.

14. The method of claim 8, further comprising:
receiving a stimuli timing signal containing timing information corresponding to one or both of the visual stimulus and the auditory stimulus.

15. A transit gate comprising:
a gate receiver configured to receive wireless signals from a wearable electronic device, wherein the wearable electronic device includes an electroencephalography (EEG) sensor configured to detect EEG signals corresponding to a transit user;
a display system configured to display a visual stimulus, wherein the wearable electronic device is configured to determine that the transit user is attempting to enter a transit system through the transit gate based on a first EEG signal detected by the EEG sensor, the first EEG signal based at least in part on the transit user viewing the visual stimulus;
an audio system configured to output an auditory stimulus, wherein the wearable electronic device is configured to determine that the transit user is passing through the transit gate based on a second EEG signal detected by the EEG sensor, the second EEG signal based at least in part on the transit user hearing the auditory stimulus; and
a gate processor configured to perform operations comprising:
receiving, via the gate receiver from the wearable electronic device, a first wireless signal indicating that the transit user is attempting to enter the transit system through the transit gate; and
receiving, via the gate receiver from the wearable electronic device, a second wireless signal indicating that the transit user is passing through the transit gate.

16. The transit gate of claim 15, wherein the operations further comprise:
in response to receiving the second wireless signal, allowing the transit user to enter the transit system by removing a physical barrier associated with the transit gate.

17. The transit gate of claim 15, wherein the first wireless signal is received concurrently with the second wireless signal.

18. The transit gate of claim 15, wherein the operations further comprise:
outputting, via the audio system, the auditory stimulus.

19. The transit gate of claim 18, wherein the auditory stimulus is outputted in response to receiving the first wireless signal.

20. The transit gate of claim 15, wherein the operations further comprise:
receiving a stimuli timing signal containing timing information corresponding to one or both of the visual stimulus and the auditory stimulus.

\* \* \* \* \*